(12) United States Patent
Omenetto et al.

(10) Patent No.: US 11,833,272 B2
(45) Date of Patent: Dec. 5, 2023

(54) SILK-FIBROIN HYDROGELS, METHODS OF FORMING, AND USES THEREOF

(71) Applicant: Trustees of Tufts College, Medford, MA (US)

(72) Inventors: Fiorenzo G. Omenetto, Lexington, MA (US); Matthew B. Applegate, Somerville, MA (US); David L. Kaplan, Concord, MA (US)

(73) Assignee: Trustees of Tufts College, Medford, MA (US)

( * ) Notice: Subject to any disclaimer, the term of this patent is extended or adjusted under 35 U.S.C. 154(b) by 1487 days.

(21) Appl. No.: 16/063,479

(22) PCT Filed: Dec. 16, 2016

(86) PCT No.: PCT/US2016/067269
§ 371 (c)(1),
(2) Date: Jun. 18, 2018

(87) PCT Pub. No.: WO2017/123383
PCT Pub. Date: Jul. 20, 2017

(65) Prior Publication Data
US 2020/0069845 A1 Mar. 5, 2020

Related U.S. Application Data

(60) Provisional application No. 62/268,993, filed on Dec. 17, 2015.

(51) Int. Cl.
*A61L 27/52* (2006.01)
*A61L 27/48* (2006.01)

(52) U.S. Cl.
CPC ............... *A61L 27/52* (2013.01); *A61L 27/48* (2013.01); *A61L 2400/06* (2013.01); *A61L 2430/16* (2013.01)

(58) Field of Classification Search
CPC ...... A61L 27/52; A61L 27/48; A61L 2400/06; A61L 2430/16
See application file for complete search history.

(56) References Cited

U.S. PATENT DOCUMENTS

| | | | |
|---|---|---|---|
| 5,245,012 A | 9/1993 | Lombari | |
| 8,247,384 B2 | 8/2012 | Green | |
| 2004/0067503 A1 | 4/2004 | Tan | |

FOREIGN PATENT DOCUMENTS

| | | |
|---|---|---|
| WO | 1997008315 | 3/1997 |
| WO | 2004080346 | 9/2004 |
| WO | 2005012606 | 2/2005 |
| WO | 2005123114 | 12/2005 |
| WO | 2007016524 | 2/2007 |
| WO | 2008118133 | 10/2008 |
| WO | 2008150861 | 12/2008 |
| WO | 2015054125 | 4/2015 |

OTHER PUBLICATIONS

Shen et al., "Photodynamic cross-linking of proteins V. Nature of the tyrosine-tyrosine bonds formed in the FMN-sensitized intermolecular cross-linking of N-acetyl-L-tyrosine"; 2000, Journal of Photochemistry and Photobiology A: Chemistry 133, pp. 115-122.*
Altman, G. H., et al. "Silk-based biomaterials." Biomaterials 24.3 (2003): 401-416.
Applegate, M. B., et al. "Biocompatible silk step-index optical waveguides." Biomedical optics express 6.11 (2015):4221-4227.
Bini, E. et al. "Mapping domain structures in silks from insects and spiders related to protein assembly." Journal of molecular biology335.1 (2004): 27-40.
Chao, P-H G, et al. "Silk hydrogel for cartilage tissue engineering." Journal of Biomedical Materials Research Part B: Applied Biomaterials 95.1 (2010): 84-90.
Chirila, T. V., et al. "Silk as substratum for cell attachment and proliferation." Materials Science Forum. vol. 561. Trans Tech Publications, 2007.
Chirila, T. V., et al. "Zainuddin; Harkin, DG; Schwab, IR; Hirst, LW Bombyx mori silk fibroin membranes as potential substrata for epithelial constructs used in the management of ocular surface disorders." Tissue Eng. Part A14 (2008): 1203-1211.
Choi, M., et al. "Light-guiding hydrogels for cell-based sensing and optogenetic synthesis in vivo." Nature photonics 7.12 (2013): 987.
Choi, Y. et al. "A fully biocompatible single-mode distributed feedback laser." Lab on a Chip 15.3 (2015): 642-645.
Dixon, J. M., et al. "PhotochemCAD 2: A Refined Program with Accompanying Spectral Databases for Photochemical Calculations." Photochemistry and photobiology 81.1 (2005): 212-213.
Drury, J. L., et al. "Hydrogels for tissue engineering: scaffold design variables and applications." Biomaterials 24.24 (2003): 4337-4351.
Gil, E. S., et al. "Helicoidal multi-lamellar features of RGD-functionalized silk biomaterials for corneal tissue engineering." Biomaterials 31.34 (2010): 8953-8963.
Gil, E. S., et al. "Response of human corneal fibroblasts on silk film surface patterns." Macromolecular bioscience 10.6 (2010): 664-673.
Guziewicz, N, et al. "Lyophilized silk fibroin hydrogels for the sustained local delivery of therapeutic monoclonal antibodies." Biomaterials 32.10 (2011): 2642-2650.
Han Ang, W., et al. "Classical and non-classical ruthenium-based anticancer drugs: Towards targeted chemotherapy." European Journal of Inorganic Chemistry 2006.20 (2006): 4003-4018.
Harkin, D. G., et al. "Silk fibroin in ocular tissue reconstruction." Biomaterials 32.10 (2011): 2445-2458.
Higa, K. et al. "Recent advances in cultivated epithelial transplantation." Cornea 27 (2008): S41-S47.

(Continued)

*Primary Examiner* — Shirley V Gembeh
(74) *Attorney, Agent, or Firm* — GTC Law Group PC & Affiliates

(57) ABSTRACT

The present disclosure provides transparent, elastic silk hydrogels for applications, including corneal reshaping to restore visual acuity and photolithography. The present disclosure also provides methods of photocrosslinking silk fibroin protein using riboflavin as a photoinitiator and exposing such riboflavin doped silk fibroin to light resulting in the formation of a transparent, elastic hydrogel.

10 Claims, 4 Drawing Sheets

(56) References Cited

OTHER PUBLICATIONS

Hopkins, A. M., et al. "Silk hydrogels as soft substrates for neural tissue engineering." Advanced functional materials 23.41 (2013): 5140-5149.

Hunter, EPL, et al. "The effect of oxygen, antioxidants, and superoxide radical on tyrosine phenoxyl radical dimerization." Free Radical Biology and Medicine 6.6 (1989): 581-585.

Busuki, S., et al. "Photochemically cross-linked collagen gels as three-dimensional scaffolds for tissue engineering." Tissue engineering 13.8 (2007): 1995-2001.

International Searching Authority, International Search Report and Written Opinion for PCT/US2016/067269, 12 pages, dated Jul. 21, 2017.

Jin, H-J, et al. "Mechanism of silk processing in insects and spiders." Nature 424.6952 (2003): 1057.

Kato, Y. et al. "Aggregation of collagen exposed to UVA in the presence of riboflavin: a plausible role of tyrosine modification." Photochemistry and photobiology 59.3 (1994): 343-349.

Kikuchi, KM et al., "Structure of the Bombyx mori fibroin light-chain-encoding gene: upstream sequence elements common to the light and heavy chain," 110 Gene, 151-158 (1992).

Kim, S., et al. "All-water-based electron-beam lithography using silk as a resist." Nature nanotechnology 9.4 (2014): 306.

Kim, S., et al. "Silk inverse opals." Nature Photonics 6.12 (2012): 818.

Kim, S-H, et al. "Fabrication of a biodegradable polysaccharide hydrogel with riboflavin, vitamin B2, as a photo-initiator and L-arginine as coinitiator upon UV irradiation." Journal of Biomedical Materials Research Part B: Applied Biomaterials 91.1 (2009): 390-400.

Kim, U.-J., et al. "Structure and properties of silk hydrogels." Biomacromolecules 5.3 (2004): 786-792.

Lawrence, B. D., et al. "Human corneal limbal epithelial cell response to varying silk film geometric topography in vitro." Acta biomaterialia 8.10 (2012): 3732-3743.

Lawrence, B. D., et al. "Silk film biomaterials for cornea tissue engineering." Biomaterials 30.7 (2009): 1299-1308.

Lucas, F., J. et al. "The silk fibroins." Advances in protein chemistry. vol. 13. Academic Press, 1958. 107-242.

Marquez, L. A., et al. "Kinetics of Oxidation of Tyrosine and Dityrosine by Myeloperoxidase Compounds I and II Implications for lipoprotein peroxidation studies." Journal of Biological Chemistry 270.51 (1995): 30434-30440.

Masurovsky, E. B., et al. "Photo-reconstituted collagen gel for tissue culture substrates." Experimental cell research 76.2 (1973): 447-148.

Mccall, A. S., et al. "Mechanisms of corneal tissue cross-linking in response to treatment with topical riboflavin and long-wavelength ultraviolet radiation (UVA)." Investigative ophthalmology & visual science 51.1 (2010): 129-138.

Mondia, JP, et al. "Rapid nanoimprinting of doped silk films for enhanced fluorescent emission." Advanced Materials 22.41 (2010): 4596-4599.

Nagarkar, S., et al. "Structure and gelation mechanism of silk hydrogels." Physical Chemistry Chemical Physics 12.15 (2010): 3834-3844.

Nguyen, A. K., et al. "Two-photon polymerization of polyethylene glycol diacrylate scaffolds with riboflavin and triethanolamine used as a water-soluble photoinitiator." Regenerative medicine 8.6 (2013): 725-738.

Omenetto, F. G., et al. "A new route for silk." Nature Photonics 2 (2008): 641-643.

Omenetto, F. G., et al. "New opportunities for an ancient material." Science 329.5991 (2010): 528-531.

Parker, S. T., et al. "Biocompatible silk printed optical waveguides." Advanced Materials 21.23 (2009): 2411-2415.

Partlow, B. P., et al. "Highly tunable elastomeric silk biomaterials." Advanced functional materials 24.29 (2014): 4615-4624.

Peppas, N. A., et al. "Hydrogels in biology and medicine: from molecular principles to bionanotechnology." Advanced materials 18.11 (2006): 1345-1360.

Randleman, JB et al. "Lasik interface complications: etiology, management, and outcomes." Journal of Refractive Surgery 28.8 (2012): 575-586.

Rockwood, DN, et al. "Materials fabrication from Bombyx mori silk fibroin." Nature protocols 6.10 (2011): 1612.

Sashina, E. S., et al. "Structure and solubility of natural silk fibroin." Russian Journal of Applied Chemistry 79.6 (2006): 869-876.

Silva, E, et al. "Visible light anaerobic photoconversion of tyrosine sensitized by riboflavin. Cytotoxicity on mouse tumoral cells." Photochemistry and photobiology 62.6 (1995): 1041-1045.

Srinivasan, R., et al. "Ultraviolet laser ablation of organic polymers." Chemical Reviews 89.6 (1989): 1303-1316.

Takei, F., et al. "Further evidence for importance of the subunit combination of silk fibroin in its efficient secretion from the posterior silk gland cells." The Journal of cell biology 105.1 (1987): 175-180.

Tanaka, K., et al. "Determination of the site of disulfide linkage between heavy and light chains of silk fibroin produced by Bombyx mori." Biochimica et Biophysica Acta (BBA)—Protein Structure and Molecular Enzymology 1432.1 (1999): 92-103.

Tanaka, K., et al. "Immunological identification of the major disulfide-linked light component of silk fibroin." The Journal of Biochemistry 114.1 (1993): 1-4.

Tao, H et al. "Silk materials—a road to sustainable high technology." Advanced materials 24.21 (2012): 2824-2837.

Toffanin, S, et al. "Low-threshold blue lasing from silk fibroin thin films." Applied Physics Letters 101.9 (2012): 091110.

Tsubouchi, K, et al. "Bombyx mori fibroin enhanced the proliferation of cultured human skin fibroblasts." Journal of Insect Biotechnology and Sericology 72.1 (2003): 65-69.

Whittaker, J. L., et al. "Facile and rapid ruthenium mediated photo-crosslinking of Bombyx mori silk fibroin." Journal of Materials Chemistry B 2.37 (2014): 6259-6270.

Wollensak, G. et al. "Riboflavin/ultraviolet-A-induced collagen crosslinking for the treatment of keratoconus." American journal of ophthalmology 135.5 (2003): 620-627.

Wray, L. S., et al. "Effect of processing on silk-based biomaterials: Reproducibility and biocompatibility." Journal of Biomedical Materials Research Part B: Applied Biomaterials 99.1 (2011): 89-101.

Wu, J., et al. "Corneal stromal bioequivalents secreted on patterned silk substrates." Biomaterials 35.12 (2014): 3744-3755.

Yildirim, A., et al. "Corneal collagen crosslinking for ectasia after laser in situ keratomileusis: long-term results." Journal of Cataract & Refractive Surgery 40.10 (2014): 1591-1596.

Zhu, J. et al. "Design properties of hydrogel tissue-engineering scaffolds." Expert review of medical devices 8.5 (2011): 607-626.

* cited by examiner

SILK-FIBROIN HYDROGELS, METHODS OF FORMING, AND USES THEREOF

CROSS-REFERENCE TO RELATED APPLICATIONS

This application represents the national stage entry of International Application PCT/US2016/067269 filed Dec. 16, 2016, which claims the benefit of U.S. Provisional Patent Application 62/268,993, filed Dec. 17, 2015, the contents of which is hereby incorporated by reference in its entirety for all purposes herein.

GOVERNMENT SUPPORT

This invention was made with government support under grant N00014-13-1-0596 awarded by the Office of Naval Research. The government has certain rights in the invention.

BACKGROUND

Silk fibroins produced from the silks of silkworms and orb-weaving spiders have desirable properties, for example, mechanical properties, optical properties, etc. Silk fibroins have numerous attractive characteristics, including: the ability to stabilize labile compounds, biocompatibility, biodegradability, cytocompatibility, mechanical strength, and transparency.

SUMMARY

The present disclosure provides, among other things, silk fibroin hydrogels. Provided silk fibroin hydrogels are useful, for example, for tissue implant applications including for example, ocular prosthesis. The present disclosure also provides methods of preparing and utilizing such hydrogels.

In some embodiments, silk fibroin hydrogels of the present disclosure are provided, prepared, and/or manufactured from solutions of silk fibroin.

In some embodiments, silk fibroin hydrogels of the present disclosure are provided, prepared, and/or manufactured from a silk fibroin solution of about 0.1 wt % polymer to about 30 wt % polymer. In some embodiments, silk fibroin hydrogels of the present disclosure are provided, prepared, and/or manufactured from a silk fibroin solution that is less than about 30 wt % polymer. In some embodiments, silk fibroin hydrogels of the present disclosure are provided, prepared, and/or manufactured from a silk fibroin solution that is less than about 20 wt % polymer. In some embodiments, silk fibroin hydrogels of the present disclosure are provided, prepared, and/or manufactured from a silk fibroin solution that is less than about 10 wt % polymer. Indeed, in some embodiments, the present disclosure provides the surprising teaching that useful silk fibroin hydrogels with particularly valuable properties can be provided, prepared, and/or manufactured from a silk fibroin solution that is less than about 10 wt % polymer, or even that is about 5% wt %, about 4 wt %, about 3 wt %, about 2 wt %, about 1 wt % polymer or less.

In some embodiments, methods of providing, preparing, and/or manufacturing silk fibroin hydrogels of the present disclosure include providing a flavin compound. In some embodiments, a flavin compound is or includes for example riboflavin, flavin-mononucleotide (FMN), flavin adenine dinucleotide (FAD).

In some embodiments, a flavin compound is in solution. In some embodiments, a solvent is or includes water. In some embodiments, a flavin compound has a concentration of about 0.2 mM to about 20 mM.

In some embodiments, methods of providing, preparing, and/or manufacturing silk fibroin hydrogels of the present disclosure include blending, combining, or mixing a silk fibroin solution with a flavin compound.

In some embodiments, methods of providing, preparing, and/or manufacturing silk fibroin hydrogels includes exposing a combination of a silk fibroin and a flavin compound to visual light. In some embodiments, methods of providing, preparing, and/or manufacturing silk fibroin hydrogels includes an exposure period. In some embodiments, an exposure period is between a few seconds and a day. In some embodiments, an exposure period is between about 5 minutes and 300 minutes. In some embodiments, an exposure period is about 60 minutes.

In some embodiments, methods of providing, preparing, and/or manufacturing silk fibroin hydrogels includes exposing a combination of a silk fibroin and a flavin compound to visual light. In some embodiments, visible light is about 330 nm to about 750 nm. In some embodiments, visible light is blue light. In some embodiments, visible light is about 350 nm to about 450 nm.

In some embodiments, methods of providing, preparing, and/or manufacturing silk fibroin hydrogels includes inducing formation of crosslinks in silk fibroin.

In some embodiments, methods of providing, preparing, and/or manufacturing silk fibroin hydrogels in accordance with the present disclosure includes photolytically introducing crosslinks.

In some embodiments, methods of providing, preparing, and/or manufacturing silk fibroin hydrogels includes photoexciting a flavin compound, for example, photoexciting riboflavin. In some embodiments, a photoexcited flavin compound, such as photoexcited riboflavin, is exposed to silk fibroin in a combined solution or pre-gel. In some embodiments, a photoexcited flavin compound strips electrons from amino acid residue side chains, such as tryosine residues. In some embodiments, tyrosine radicals form dityrosine complexes, thereby inducing formation of crosslinks, photocrosslinks in silk fibroin. In some embodiments, photocrosslinking includes radical formation due to singlet oxygen production.

In some embodiments, methods of providing, preparing, and/or manufacturing silk fibroin hydrogels of the present disclosure further include forming crosslinks utilizing amino acid residue side chains (e.g., phenolic side chains) present within polymers (e.g., protein polymers). In some embodiments, methods of providing, preparing, and/or manufacturing silk fibroin hydrogels of the present disclosure include forming crosslinks via tyrosine residues to form dityrosine covalent bonds. In some embodiments, crosslinking may include functionalization, for example, an addition of a phenol group.

In some embodiments, methods of providing, preparing, and/or manufacturing silk fibroin hydrogels in accordance with the present disclosure includes gelation. In some embodiments, gelation is initiated on combining a silk fibroin solution, a flavin compound solution, and exposure to visible light. In some embodiments, a gelation reaction forming a silk fibroin hydrogel is complete between about 20 seconds and about 5000 seconds after gelation is induced.

In some embodiments, methods of providing, preparing, and/or manufacturing silk fibroin hydrogels of the present disclosure includes providing a silk solution. In some embodiments silk includes tyrosine side chains. In some embodiments, a method of providing, preparing, and/or manufacturing silk fibroin hydrogels of the present disclosure includes boiling silk in $Na_2CO_3$ for about 10 minutes, about 20 minutes, about 30 minutes, or about 60 minutes. In some embodiments, silk fibers were solubilized in lithium bromide (LiBr) and then dialyzed against water to yield a polymer molecular weight of between about 10 kDa and about 400 kDa and a polymer concentration of between about 0.1 wt % and about 30 wt %. In some embodiments, a method of providing, preparing, and/or manufacturing silk fibroin hydrogels of the present disclosure includes adding a solution of horseradish peroxidase to the silk solution. In some embodiments, a method of providing, preparing, and/or manufacturing silk fibroin hydrogels of the present disclosure includes adding hydrogen peroxide to the combined solution of silk and horseradish peroxidase, thereby inducing gelation.

In some embodiments, silk fibroin hydrogels of the present disclosure are provided, prepared, and/or manufactured from a solution having a molecular weight in the range of about 20 kD-about 400 kD. In some embodiments, provided, prepared, and/or manufactured silk fibroin hydrogels of the present disclosure are included of polymers (e.g., protein polymers) having molecular weights within a range between a lower bound (e.g., about 20 kD, about 30 kD, about 40 kD, about 50 kD, about 60 kD, or more) and an upper bound (e.g., about 400 kD, about 375 kD, about 350 kD, about 325 kD, about 300 kD, or less).

In some particular embodiments, silk fibroin hydrogels of the present disclosure are provided, prepared, and/or manufactured from a solution of silk fibroin that has been boiled and/or degummed to remove sericin for at least about 5, 10, 15, 20, 25, 30, 35, 40, 45, 50, 55, 60, 70, 80, 90, 100, 110, 120, 150, 180, 210, 240, 270, 310, 340, 370, 410 minutes or more. In some embodiments, such degumming is performed at a temperature within the range of: about 30° C., about 35° C., about 40° C., about 45° C., about 50° C., about 45° C., about 60° C., about 65° C., about 70° C., about 75° C., about 80° C., about 85° C., about 90° C., about 95° C., about 100° C., about 105° C., about 110° C., about 115° C., about at least 120° C. In some embodiments, such degumming is performed at a temperature below about 65° C. In some embodiments, such degumming is performed at a temperature of about 60° C. or less.

In some embodiments, silk fibroin hydrogels of the present disclosure are provided, prepared, and/or manufactured from a silk fibroin solution that is adjusted to (e.g., by dialysis) and/or maintained at a sub-physiological pH (e.g., at or below a pH significantly under pH 7). For example, in some embodiments, silk fibroin hydrogels of the present disclosure are provided, prepared, and/or manufactured from a silk fibroin solution that is adjusted to and/or maintained at a pH near or below about 6. In some embodiments, silk fibroin hydrogels are provided, prepared, and/or manufactured from a silk fibroin solution with a pH for instance about 6 or less, or about 5 or less. In some embodiments, silk fibroin hydrogels are provided, prepared, and/or manufactured from a silk fibroin solution with a pH in a range for example of at least 6, at least 7, at least 8, at least 9, and at least about 10.

In some embodiments, silk fibroin hydrogels of the present disclosure are provided, prepared, and/or manufactured from a silk fibroin solution where the solvent is water, PBS and combinations thereof. In some embodiments, silk fibroin hydrogels of the present disclosure are provided, prepared, and/or manufactured from a silk fibroin solution in a solvent other than PBS. In some embodiments, silk fibroin hydrogels of the present disclosure are provided, prepared, and/or manufactured from an aqueous silk fibroin solution. In some embodiments, silk fibroin hydrogels of the present disclosure are provided, prepared, and/or manufactured from a silk fibroin solution in DMEM. In some embodiments, silk fibroin hydrogels of the present disclosure are provided, prepared, and/or manufactured from an aqueous protein polymer solution that is not buffered.

In some embodiments, solutions further include protein polymers such as agarose, alginate, cellulose, chitin, chitosan, collagen, elastin, gelatin, hyaluronic acid, polydimethylsiloxane, poly(ethylene glycol), polyhydroxyalkanoates, poly(lactide-co-glycolide), pullan, resilin, silk, starch, and combinations thereof.

In some embodiments, methods of providing, preparing, and/or manufacturing silk fibroin hydrogels of the present disclosure includes incorporating one or more additives, agents, and/or functional moieties. In some embodiments, a step of incorporating includes modifying silk fibroin hydrogels of the present disclosure with one or more additives, agents, and/or functional moieties. In some embodiments, a step of incorporating occurs prior to gelation. In some embodiments, a step of incorporating occurs after to gelation. For example, in some embodiments, a step of incorporating a biological and/or biologically active agent can occur before or after before gelation is induced, during gelation, or after gelation and/or photocrosslinking has completed. In some embodiments, methods of using silk fibroin hydrogels of the present disclosure includes adhering cells to a surface of silk fibroin hydrogels. In some embodiments, a method of using silk fibroin hydrogels of the present disclosure includes encapsulating cells within a matrix silk fibroin hydrogels. In some embodiments, a method of using silk fibroin hydrogels of the present disclosure includes encapsulating cells for introducing cells to a native tissue.

In some embodiments, mechanical properties provide an indication of resilience and/or elasticity between silk fibroin hydrogels and a native tissue. In some embodiments, a method of providing, preparing, and/or manufacturing silk fibroin hydrogels of the present disclosure includes matching, tuning, adjusting, and/or manipulating mechanical properties of silk fibroin hydrogels of the present disclosure. In some embodiments, silk fibroin hydrogels are matched for use with corneal tissue. In some embodiments, mechanical properties include, for example, storage modulus, tangent modulus, plateau modulus, swelling, and/or dynamic modulus.

In some embodiments, matching, tuning, adjusting, and/or manipulating mechanical properties of silk fibroin hydrogels include controlling, for example: by selecting a molecular weight of a silk fibroin, by selecting a concentration of a silk fibroin solution, by selecting a specific flavin compound, by selecting a specific flavin compound concentration, by selecting a specific wavelength, by adjusting exposure time, optical power, or power density, and by combinations thereof.

In some embodiments, matching, tuning, adjusting, and/or manipulating mechanical properties of silk fibroin hydrogels of the present disclosure is accomplished, at least in part, by selecting a molecular weight of a polymer. In some embodiments, a molecular weight of a polymer is in a range of molecular weights between about 10 kDa and about 400 kDa.

In some embodiments, matching, tuning, adjusting, and/or manipulating mechanical properties of silk fibroin hydrogels of the present disclosure is accomplished, at least in part, by selecting a polymer solution concentration. In some embodiments, a polymer solution concentration is in a range of concentrations between about 0.1 wt % and about 30 wt %.

In some embodiments, silk fibroin hydrogels of the present disclosure can be highly tunable with mechanical moduli, for example, ranging from approximately 2 kPa up to 300 to 400 kPa with gelation times in the seconds to minutes range.

In some embodiments, silk fibroin hydrogels formed by methods described herein are elastic or highly elastic hydrogels. In some embodiments, silk fibroin hydrogels as provided herein are able to withstand 100% strain or greater in shear. Additionally or alternatively, in some embodiments, silk fibroin hydrogels are able to withstand 50% strain or greater in compression.

In some embodiments, silk fibroin hydrogels formed by methods described herein can have tunable mechanical properties. For example, hydrogels can have moduli between 200 Pa up to 15 kPa without post-treatment and gels with compressive moduli on the order of 100+ kPa after treatment with methanol.

In some embodiments, silk fibroin hydrogels formed by methods described herein can have unique swelling properties. For example, photocrosslinked silk fibroin hydrogels described herein can have up to 400% swelling, making them excellent candidates for various applications. In some embodiments, silk fibroin hydrogels with high swelling properties can be used to deliver agents including, but not limited to, drugs, growth factors, antibodies, etc.

In some embodiments, crosslink density correlates with hydrogel stiffness. In some embodiments, an increase in hydrogel stiffness correlates with an increase in crosslink density. In some embodiments, an increase in hydrogel stiffness of about 25× to about 125× correlates with an increase in crosslink density about 2× to about 10×.

In some embodiments, silk fibroin hydrogels formed by methods described herein can be injectable. Without wishing to be bound by theory, low viscosity constituents allow for ease of injection. While silk hydrogel produced in the presence of an electric current as discussed previously (also known as an "e-gel") is elastic, the silk hydrogel requires application of current.

In some embodiments, silk fibroin hydrogels formed by methods described herein can be adhesive. For example, silk fibroin hydrogels can adhere to a surface, e.g., a metal surface such as a stainless steel plate. In some embodiments, silk fibroin hydrogels adhere to a tissue. In some embodiments, silk fibroin hydrogels adhere to corneal tissue.

In some embodiments, silk fibroin hydrogels formed by methods described herein can be optically clear. For example, silk fibroin hydrogels exhibit negligible absorbance above 290 nm. Optical clarity allows for various application, e.g., optical machining, cell imaging within and through the gels and/or other applications that other opaque hydrogels do not permit.

In some embodiments, ocular prosthesis are provided, prepared, and/or manufactured including providing a mixture comprising silk fibroin and a flavin compound; contacting the mixture to corneal tissue; and exposing the mixture and the corneal tissue to visible light to induce formation of dityrosine crosslinks in the silk fibroin, thereby forming a silk fibroin gel and adhering the gel to the corneal tissue.

In some embodiments, a silk solution or a flavin compound solution, or a mixture thereof is dried or partially dried prior to exposure.

In some embodiments, a mixture is gelled or partially gelled prior to contacting.

In some embodiments, ocular prosthesis are provided, prepared, and/or manufactured including providing a silk fibroin solution and a riboflavin solution, applying a mixture or combination on a surface of the biopolymer hydrogel; contacting an applied surface of a biopolymer hydrogel to corneal tissue, thereby creating an interface; exposing the interface to visible light to induce formation of dityrosine crosslinks in the silk fibroin, thereby forming a silk fibroin gel and adhering the silk fibroin gel to the corneal tissue and to the biopolymer hydrogel.

In some embodiment, ocular prosthesis formed according to methods provided herein are characterized it that they recovers from a shear strain of at least 100% without showing an indication of a plastic deformation; substantially transparent to wavelengths above 200 nm; exhibits negligible absorbance above 290 nm so that it is optically clear; recovers from a compressive strain of at least 75% without showing an indication of a plastic deformation; a storage modulus value that is between about 50 Pa and about 100 kPa; a tangent modulus of about 200 Pa to about 400 kPa; configured to be injectable; a thickness that is substantially maintained with rinsing, and/or substantially adheres to corneal tissue with rinsing.

In some embodiments, silk fibroin hydrogels formed by methods described herein are biocompatible. For example, such hydrogels have no cytotoxicity or any adverse or negative effects on the cells or tissues of a subject.

In some embodiments, silk fibroin hydrogels of the present disclosure are characterized by optical transparency, elasticity, highly tunable mechanical properties, and/or adherence to corneal collagen. That is, the present disclosure provides technologies that permit production and use of silk fibroin hydrogels, for example as an ocular prosthesis whose mechanical properties are tuned to a particular desired range and/or set. In some embodiments, silk fibroin hydrogels of the present disclosure are characterized by particular degradation properties. In some embodiments, silk fibroin hydrogels of the present disclosure degrade to release an agent useful for treatment of a disease, disorder, or condition. In some embodiments, silk fibroin hydrogels of the present disclosure are characterized by mechanical properties (e.g., optical transparency, pore size, strength [e.g., as assessed by storage modulus], flexibility, stiffness, etc.) that are particularly suitable for use as an ocular prosthesis.

In some embodiments, silk fibroin hydrogels of the present disclosure include polymers. In some embodiments, hydrogels of the present disclosure include protein polymers. In some embodiments, useful protein polymers are selected from the group consisting of agarose, alginate, cellulose, chitin, chitosan, collagen, elastin, gelatin, hyaluronic acid, polydimethylsiloxane, poly(ethylene glycol), polyhydroxyalkanoates, poly(lactide-co-glycolide), pullan, resilin, silk, starch, and combinations thereof.

In some embodiments, provided silk fibroin hydrogels are included of low molecular weight polymers, for example in that the hydrogels are substantially free of, and/or are prepared from solutions that are substantially free of, polymers having a molecular weight above about 400 kDa. In some embodiments, the highest molecular weight polymers in provided hydrogels are less than about 300 kDa-about 400 kDa (e.g., less than about 400 kDa, less than about 375 kDa, less than about 350 kDa, less than about 325 kDa, less than about 300 kDa, etc.). In some embodiments, provided hydrogels are included of polymers (e.g., protein polymers) having molecular weights within the range of about 20 kDa-about 400 kDa. Those skilled in the art will appreciate that, typically, when a provided hydrogel is said to include a particular polymer of a specified molecular weight (including within a specified molecular weight range), the hydrogel is substantially free of other molecular weight species of that polymer.

In some embodiments, provided hydrogels are biocompatible. In some embodiments, provided hydrogels are biodegradable. In some embodiments, provided hydrogels are biocompatible and biodegradable.

In some embodiments, silk fibroin for use in practice of the present disclosure includes amino acid residues with phenolic side chains. In some embodiments, such amino acid residues include tyrosines. In some embodiments, provided silk fibroin hydrogels include covalently crosslinked protein polymers. In some embodiments, such hydrogels include crosslinks that utilize amino acid residue side chains (e.g., phenolic side chains). In some embodiments, provided hydrogels include photocrosslinked silk fibroin hydrogel. In some embodiments, polymers in such provided silk fibroin hydrogels are cross-linked via tyrosine residues. In some embodiments, crosslinks in provided hydrogels are or include dityrosine covalent bonds.

In some embodiments, provided silk fibroin hydrogels are characterized by crystalline structure, for example, comprising beta sheet structure and/or hydrogen bonding. In some embodiments, provided hydrogels are characterized by a percent beta sheet structure within the range of about 0% to about 45%.

In some embodiments, provided silk fibroin hydrogels are characterized by an ability to recover from strain and/or compression.

In some embodiments, provided silk fibroin hydrogels are characterized by high elasticity. Elasticity or elastic deformation generally measures a tendency of a material to return to its original size and/or shape after a force having been applied to the material and having deformed the material is subsequently removed. In contrast, plastic deformation follows application of enough stress on a material to cause a change in the size and/or shape of the material in a way that is not reversible, such that the material does not return to its original size and/or shape. A plastic deformation specifically involves a change to the structure of the material, such as a molecular and/or atomic shift or dislocation from which the material cannot recover. In some embodiments, provided silk fibroin hydrogels of the present disclosure are characterized as having a tangent modulus value between about 200 Pa to about 400 kPa without showing an indication of a plastic deformation. In some embodiments, photocrosslinked silk fibroin hydrogels of the present disclosure are characterized in that they recover from a compressive strain of at least 75% while resisting degradation and without showing evidence of a plastic deformation.

In some embodiments, silk fibroin hydrogels of the present disclosure are characterized in that they recover from a shear strain of at least 100% while resisting degradation and without showing evidence of a plastic deformation.

In some embodiments, provided silk fibroin hydrogels are characterized by a desired high storage modulus value. In some embodiments, a high storage modulus value corresponds with a strong and/or robust hydrogel. In some particular embodiments exemplified herein, provided silk fibroin hydrogels are characterized by a storage modulus value between about 50 Pa and about 100 kPa without showing an indication of a plastic deformation. In some particular embodiments exemplified herein, provided silk fibroin hydrogels are characterized by a storage modulus value great than about 1 kPa without showing an indication of a plastic deformation.

In some embodiments, provided silk fibroin hydrogels having a high storage modulus value are characterized in that they are formed from solutions that have a low weight percent polymer concentration.

In some embodiments, provided silk fibroin hydrogels are characterized by a high resiliency. Resiliency provides an indication of an ability of a material to absorb energy when a force is applied and the material is deformed and subsequently release energy when the force is removed permitting the material to return to its natural state. In some embodiments, provided silk fibroin hydrogels of the present disclosure are characterized as highly resilient to a repetitive force with high cycle. In some embodiments, a high cycle is at least 3,600 cycles at a frequency 0.5 Hz. In some embodiments, silk fibroin hydrogels of the present disclosure are characterized in that they recover from exposure to a compressive strain of at least 10% at a high cycle without showing evidence of a plastic deformation. In some embodiments, silk fibroin hydrogels of the present disclosure are characterized in that they recover from exposure to a shear strain of at least 10% at a high cycle without showing evidence of a plastic deformation.

In some embodiments, silk fibroin hydrogels of the present disclosure are characterized in that they swell up to 400% when exposed to solvents without showing evidence of a plastic deformation.

In some embodiments, silk fibroin hydrogels of the present disclosure are substantially transparent in the visible spectrum. In some embodiments, provided silk fibroin-based hydrogels are between about 50% and 100% transparent in the visible spectrum. In some embodiments, silk fibroin-based hydrogels are characterized by having a high degree of transparency, e.g., about 20% to 99% transmittance in the visible spectrum (wavelengths ranging between about 400-700 nm).

In some embodiments, silk fibroin hydrogels of the present disclosure are configured to support incorporation of and/or modification with one or more additive, agents, and/or functional moieties. In some embodiments, silk fibroin hydrogels of the present disclosure provide tunable mechanical properties that support encapsulation cells, for example for cell engineering and/or tissue regeneration applications including for example in the treatment or prevention of a disease, disorder or condition and/or for inducing tissue repair.

In some embodiments, encapsulation/incorporation and/or degradation characteristics of such silk fibroin hydrogels are tuned according to fabrication conditions (e.g., molecular weight of polymer, wt % of polymer in solution from which the silk fibroin hydrogel is prepared, nature and/or degree of crosslinking, nature and/or degree of modification [e.g., with one or more agents and/or functional moieties], etc.).

In some embodiments, the present disclosure includes an ocular prosthesis kit. In some embodiments, an ocular prosthesis kit includes a silk fibroin solution and a flavin solution. In some embodiments, an ocular prosthesis kit includes other biopolymers.

In some embodiments, an ocular prosthesis kit includes a combined solution, a mixture or blend of a silk fibroin solution and a flavin solution. In some embodiments, a mixture or blend of a silk fibroin solution and a flavin solution of an ocular prosthesis kit is shielded from exposure to visible light until use. In some embodiments, a flavin is riboflavin, FDA, or FMN.

In some embodiments, an ocular prosthesis kit includes a silk fibroin gel. In some embodiments, an ocular prosthesis kit includes a biopolymer gel.

In some embodiments, an ocular prosthesis kit including a mixture or blend of a silk fibroin solution and a flavin solution as disclosed herein when exposed to visible forms a gel including dityrosine crosslinks.

BRIEF DESCRIPTION OF THE DRAWING

FIG. 1 at panel [A] shows a plot of the stiffness of a silk riboflavin solution increasing under illumination (white bars) and holding steady when in darkness (black bar). Time 0 indicates when the light was removed. FIG. 1 at panel [B] shows the effect of different compounds on gelation rate after illumination for 1 hour. Shear modulus values are recorded for silk dissolved in deionized water ($H_2O$), deuterated water ($D_2O$), sodium azide (NaAz), and superoxide dismutase (SOD). Negative controls −RF and −Light were tested without riboflavin and without illumination respectively. Shear modulus is presented on a log scale. "NS" indicates a nonsignificant difference. All other pairs of values were significant with $p<0.001$. N=4 for treatment groups and N=3 for control groups. All data are plotted as points with bars representing the mean of each group. FIG. 1 at panel [C] shows fluorescence spectra of 3 solutions after 60 minutes of illumination by 450 nm light. Silk alone (black) shows no fluorescence, un-rinsed silk gels have a small dityrosine peak at 410 nm and a small riboflavin peak at 530 nm, rinsed silk gels have a strong dityrosine peak and no evidence of riboflavin fluorescence. Dark lines indicate the means of 8 samples with the standard deviations at each wavelength indicated by the shaded regions.

FIG. 3 at panel [A] shows silk thicknesses measured in 32 locations on each eye prior to application, immediately after application, following light exposure, and following a rinse with PBS. Films without riboflavin (CON) and films not exposed to light (RNL) show no ability to withstand rinsing. Riboflavin impregnated silk films exposed to light (RFL) are able to adhere to the corneal surface. All measurements are displayed. Data from individual eyes is indicated by a different shade. Heavy bars indicate the mean of all the data in that group. Stars indicate statistical significance between groups ($p<0.05$). n=6 for CON and RFL, n=4 for RNL. FIG. 3 at panel [B] shows a histologic section of eye stained with H& E showing silk (indicated by the bracket) overlaying wavy corneal collagen. Scale bar represents 100 FIG. 3 at panel [C] shows representative OCT images of silk films applied to deepithelialized enucleated porcine eyes. Top row: Riboflavin impregnated silk. Arrows with a solid black outer line indicate the layer of silk overlying the corneal collagen. Arrows with a dashed black outer line indicate air bubbles in the silk prior to illumination causing shadowing. Arrows with a dashed white outer line indicate specular reflection artifacts in the OCT image. Bottom row: Images of control film without riboflavin.

FIG. 4 at panel [A] shows porcine corneas treated with silk doped with riboflavin without light exposure. FIG. 4 at panel [B] shows porcine corneas treated with silk doped with riboflavin with light exposure.

DEFINITIONS

Figure 1:
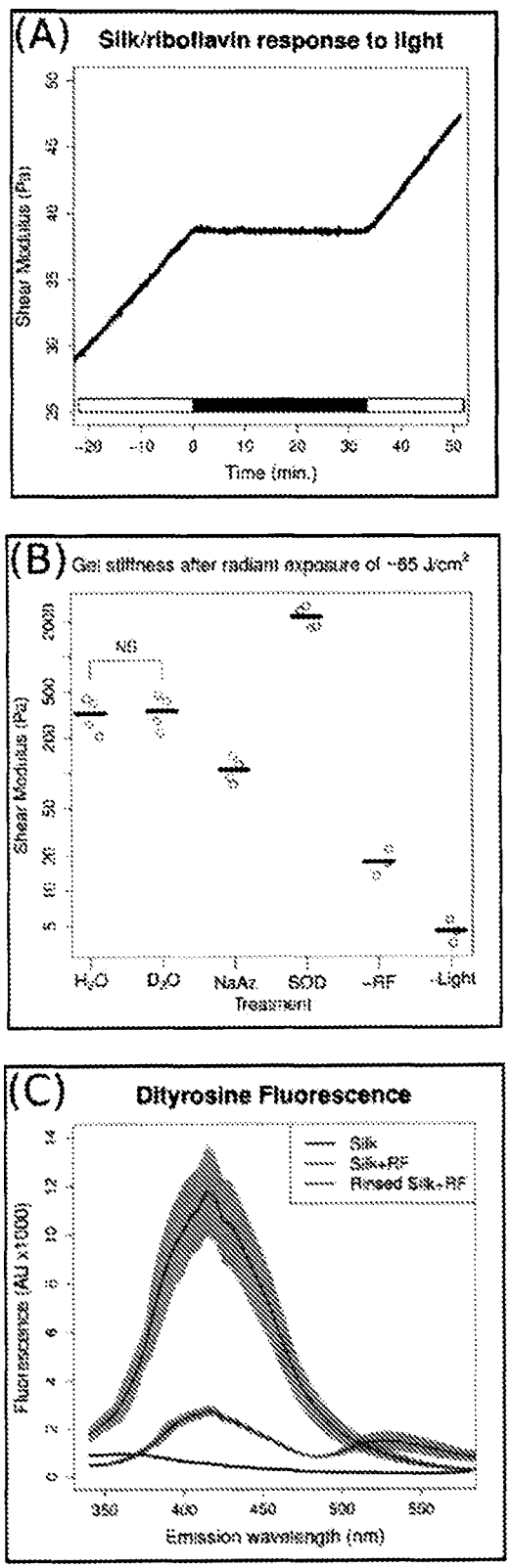
FIG. 1 Silk gelation using riboflavin.

In order for the present disclosure to be more readily understood, certain terms are first defined below. Additional definitions for the following terms and other terms are set forth throughout the specification.

In this application, unless otherwise clear from context, the term "a" may be understood to mean "at least one." As used in this application, the term "or" may be understood to mean "and/or." In this application, the terms "comprising" and "including" may be understood to encompass itemized components or steps whether presented by themselves or together with one or more additional components or steps. Unless otherwise stated, the terms "about" and "approximately" may be understood to permit standard variation as would be understood by those of ordinary skill in the art. Where ranges are provided herein, the endpoints are included. As used in this application, the term "comprise" and variations of the term, such as "comprising" and "comprises," are not intended to exclude other additives, components, integers or steps.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": As used herein, the term "administration" refers to the administration of a composition to a subject. Administration may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

"Affinity": As is known in the art, "affinity" is a measure of the tightness with a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

"Agent": As used herein, the term "agent" may refer to a compound or entity of any chemical class including, for example, polypeptides, nucleic acids, saccharides, lipids, small molecules, metals, or combinations thereof. As will be clear from context, in some embodiments, an agent can be or include a cell or organism, or a fraction, extract, or component thereof. In some embodiments, an agent is agent is or includes a natural product in that it is found in and/or is obtained from nature. In some embodiments, an agent is or includes one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present disclosure include small molecules, antibodies, antibody fragments, aptamers, siRNAs, shRNAs, DNA/RNA hybrids, antisense oligonucleotides, ribozymes, peptides, peptide mimetics, small molecules, etc. In some embodiments, an agent is or includes a polymer. In some embodiments, an agent is not a polymer and/or is substantially free of any polymer. In some embodiments, an agent contains at least one polymeric moiety. In some embodiments, an agent lacks or is substantially free of any polymeric moiety.

"Amino acid": As used herein, the term "amino acid," in its broadest sense, refers to any compound and/or substance that can be incorporated into a polypeptide chain, e.g., through formation of one or more peptide bonds. In some embodiments, an amino acid has the general structure H2N—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, and/or substitution as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" is used to refer to a free amino acid; in some embodiments it is used to refer to an amino acid residue of a polypeptide.

"Analog": As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

"Antibody": As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents included of two identical heavy chain polypeptides (about 50 kD each) and two identical light chain polypeptides (about 25 kD each) that associate with each other into what is commonly referred to as a "Y-shaped" structure. Each heavy chain is included of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is included of two domains—an amino-terminal variable (VL) domain, followed by a carboxy-terminal constant (CL) domain, separated from one another by another "switch". Intact antibody tetramers are included of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. Amino acid sequence comparisons among antibody polypeptide chains have defined two light chain (κ and λ) classes, several heavy chain (e.g., μ, γ, α, ε, δ) classes, and certain heavy chain subclasses (α1, α2, γ1, γ2, γ3, and γ4). Antibody classes (IgA [including IgA1, IgA2], IgD, IgE, IgG [including IgG1, IgG2, IgG3, IgG4], IgM) are defined based on the class of the utilized heavy chain sequences. For purposes of the present disclosure, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is monoclonal; in some embodiments, an antibody is monoclonal. In some embodiments, an antibody has constant region sequences that are characteristic of mouse, rabbit, primate, or human antibodies. In some embodiments, an antibody sequence elements are humanized, primatized, chimeric, etc., as is known in the art. Moreover, the term "antibody" as used herein, will be understood to encompass (unless otherwise stated or clear from context) can refer in appropriate embodiments to any of the art-known or developed constructs or formats for capturing antibody structural and functional features in alternative presentation. For example, in some embodiments, the term can refer to bi- or other multi-specific (e.g., zybodies, etc.) antibodies, Small Modular ImmunoPharmaceuticals ("SMIPs™"), single chain antibodies, cameloid antibodies, and/or antibody fragments. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc]

"Associated" or "Associated with": As used herein, the term "associated" or "associated with" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In some embodiments, associated entities are covalently linked to one another. In some embodiments, associated entities are non-covalently linked. In some embodiments, associated entities are linked to one another by specific non-covalent interactions (i.e., by interactions between interacting ligands that discriminate between their interaction partner and other entities present in the context of use, such as, for example. streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

"Binding": It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

"Binding agent": In general, the term "binding agent" is used herein to refer to any entity that binds to a target of interest as described herein. In many embodiments, a binding agent of interest is one that binds specifically with its target in that it discriminates its target from other potential binding partners in a particular interaction contect. In general, a binding agent may be or include an entity of any chemical class (e.g., polymer, non-polymer, small molecule, polypeptide, carbohydrate, lipid, nucleic acid, etc). In some embodiments, a binding agent is a single chemical entity. In some embodiments, a binding agent is a complex of two or more discrete chemical entities associated with one another under relevant conditions by non-covalent interactions. For example, those skilled in the art will appreciate that in some embodiments, a binding agent may include a "generic" binding moiety (e.g., one of biotin/avidin/streptaviding and/or a class-specific antibody) and a "specific" binding moiety (e.g., an antibody or aptamers with a particular molecular target) that is linked to the partner of the generic biding moiety. In some embodiments, such an approach can permit modular assembly of multiple binding agents through linkage of different specific binding moieties with the same generic binding poiety partner. In some embodiments, binding agents are or include polypeptides (including, e.g., antibodies or antibody fragments). In some embodiments, binding agents are or include small molecules. In some embodiments, binding agents are or include nucleic acids. In some embodiments, binding agents are aptamers. In some embodiments, binding agents are polymers; in some embodiments, binding agents are not polymers. In some embodiments, binding agents are non-polymeric in that they lack polymeric moieties. In some embodiments, binding agents are or include carbohydrates. In some embodiments, binding agents are or include lectins. In some embodiments, binding agents are or include peptidomimetics. In some embodiments, binding agents are or include scaffold proteins. In some embodiments, binding agents are or include mimeotopes. In some embodiments, binding agents are or include stapled peptides. In certain embodiments, binding agents are or include nucleic acids, such as DNA or RNA.

"Biocompatible": The term "biocompatible", as used herein, refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro results in less than or equal to 20% cell death, and/or their administration in vivo does not induce significant inflammation or other such adverse effects.

"Biodegradable": As used herein, the term "biodegradable" refers to materials that, when introduced into cells, are broken down (e.g., by cellular machinery, such as by enzymatic degradation, by hydrolysis, and/or by combinations thereof) into components that cells can either reuse or dispose of without significant toxic effects on the cells. In certain embodiments, components generated by breakdown of a biodegradable material are biocompatible and therefore do not induce significant inflammation and/or other adverse effects in vivo. In some embodiments, biodegradable polymer materials break down into their component monomers. In some embodiments, breakdown of biodegradable materials (including, for example, biodegradable polymer materials) involves hydrolysis of ester bonds. Alternatively or additionally, in some embodiments, breakdown of biodegradable materials (including, for example, biodegradable polymer materials) involves cleavage of urethane linkages. Exemplary biodegradable polymers include, for example, polymers of hydroxy acids such as lactic acid and glycolic acid, including but not limited to poly(hydroxyl acids), poly(lactic acid)(PLA), poly(glycolic acid)(PGA), poly(lactic-co-glycolic acid)(PLGA), and copolymers with PEG, polyanhydrides, poly(ortho)esters, polyesters, polyurethanes, poly(butyric acid), poly(valeric acid), poly(caprolactone), poly(hydroxyalkanoates, poly(lactide-co-caprolactone), blends and copolymers thereof. Many naturally occurring polymers are also biodegradable, including, for example, proteins such as albumin, collagen, gelatin and prolamines, for example, zein, and polysaccharides such as alginate, cellulose derivatives and polyhydroxyalkanoates, for example, polyhydroxybutyrate blends and copolymers thereof. Those of ordinary skill in the art will appreciate or be able to determine when such polymers are biocompatible and/or biodegradable derivatives thereof (e.g., related to a parent polymer by substantially identical structure that differs only in substitution or addition of particular chemical groups as is known in the art).

"Biologically active": As used herein, the phrase "biologically active" refers to a substance that has activity in a biological system (e.g., in a cell (e.g., isolated, in culture, in a tissue, in an organism), in a cell culture, in a tissue, in an organism, etc.). For instance, a substance that, when administered to an organism, has a biological effect on that organism, is considered to be biologically active. It will be appreciated by those skilled in the art that often only a portion or fragment of a biologically active substance is required (e.g., is necessary and sufficient) for the activity to be present; in such circumstances, that portion or fragment is considered to be a "biologically active" portion or fragment.

"Characteristic portion": As used herein, the term "characteristic portion" is used, in the broadest sense, to refer to a portion of a substance whose presence (or absence) correlates with presence (or absence) of a particular feature, attribute, or activity of the substance. In some embodiments, a characteristic portion of a substance is a portion that is found in the substance and in related substances that share the particular feature, attribute or activity, but not in those that do not share the particular feature, attribute or activity. In certain embodiments, a characteristic portion shares at least one functional characteristic with the intact substance. For example, in some embodiments, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 50, or more amino acids. In general, a characteristic portion of a substance (e.g., of a protein, antibody, etc.) is one that, in addition to the sequence and/or structural identity specified above, shares at least one functional characteristic with the relevant intact substance. In some embodiments, a characteristic portion may be biologically active.

"Comparable": The term "comparable", as used herein, refers to two or more agents, entities, situations, sets of conditions, etc. that may not be identical to one another but that are sufficiently similar to permit comparison therebetween so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

"Conjugated": As used herein, the terms "conjugated," "linked," "attached," and "associated with," when used with respect to two or more moieties, means that the moieties are physically associated or connected with one another, either directly or via one or more additional moieties that serves as a linking agent, to form a structure that is sufficiently stable so that the moieties remain physically associated under the conditions in which structure is used, e.g., physiological conditions. Typically the moieties are attached either by one or more covalent bonds or by a mechanism that involves specific binding. Alternately, a sufficient number of weaker interactions can provide sufficient stability for moieties to remain physically associated.

"Corresponding to": As used herein, the term "corresponding to" is often used to designate the position/identity of a residue in a polymer, such as an amino acid residue in a polypeptide or a nucleotide residue in a nucleic acid. Those of ordinary skill will appreciate that, for purposes of simplicity, residues in such a polymer are often designated using a canonical numbering system based on a reference related polymer, so that a residue in a first polymer "corresponding to" a residue at position 190 in the reference polymer, for example, need not actually be the 190th residue in the first polymer but rather corresponds to the residue found at the 190th position in the reference polymer; those of ordinary skill in the art readily appreciate how to identify "corresponding" amino acids, including through use of one or more commercially-available algorithms specifically designed for polymer sequence comparisons.

"Detection entity": The term "detection entity" as used herein refers to any element, molecule, functional group, compound, fragment or moiety that is detectable. In some embodiments, a detection entity is provided or utilized alone. In some embodiments, a detection entity is provided and/or utilized in association with (e.g., joined to) another agent. Examples of detection entities include, but are not limited to: various ligands, radionuclides (e.g., $^{3}$H, $^{14}$C, $^{18}$F, $^{19}$F, $^{32}$P, $^{35}$S, $^{135}$I, $^{125}$I, $^{123}$I, $^{64}$Cu, $^{187}$Re, $^{111}$In, $^{90}$Y, $^{99m}$Tc, $^{177}$Lu, $^{89}$Zr etc.) fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available.

"Determine": Many methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

"Dosage form": As used herein, the term "dosage form" refers to a physically discrete unit of a therapeutic agent for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen).

"Encapsulated": The term "encapsulated" is used herein to refer to substances that are completely surrounded by another material.

"Functional": As used herein, a "functional" biological molecule is a biological molecule in a form in which it exhibits a property and/or activity by which it is characterized. A biological molecule may have two functions (i.e., bi-functional) or many functions (i.e., multifunctional).

"Graft rejection": The term "graft rejection" as used herein, refers to rejection of tissue transplanted from a donor individual to a recipient individual. In some embodiments, graft rejection refers to an allograft rejection, where the donor individual and recipient individual are of the same species. Typically, allograft rejection occurs when the donor tissue carries an alloantigen against which the recipient immune system mounts a rejection response.

"High Molecular Weight Polymer": As used herein, the term "high molecular weight polymer" refers to polymers and/or polymer solutions included of polymers (e.g., protein polymers, such as silk) having molecular weights of at least about 200 kDa, and where no more than 30% of the silk fibroin has a molecular weight of less than 100 kDa. In some embodiments, high molecular weight polymers and/or polymer solutions have an average molecular weight of at least about 100 kDa or more, including, e.g., at least about 150 kDa, at least about 200 kDa, at least about 250 kDa, at least about 300 kDa, at least about 350 kDa or more. In some embodiments, high molecular weight polymers have a molecular weight distribution, no more than 50%, for example, including, no more than 40%, no more than 30%, no more than 20%, no more than 10%, of the silk fibroin can have a molecular weight of less than 150 kDa, or less than 125 kDa, or less than 100 kDa.

"Hydrolytically degradable": As used herein, the term "hydrolytically degradable" is used to refer to materials that degrade by hydrolytic cleavage. In some embodiments, hydrolytically degradable materials degrade in water. In some embodiments, hydrolytically degradable materials degrade in water in the absence of any other agents or materials. In some embodiments, hydrolytically degradable materials degrade completely by hydrolytic cleavage, e.g., in water. By contrast, the term "non-hydrolytically degradable" typically refers to materials that do not fully degrade by hydrolytic cleavage and/or in the presence of water (e.g., in the sole presence of water).

"Hydrophilic": As used herein, the term "hydrophilic" and/or "polar" refers to a tendency to mix with, or dissolve easily in, water.

"Hydrophobic": As used herein, the term "hydrophobic" and/or "non-polar", refers to a tendency to repel, not combine with, or an inability to dissolve easily in, water.

"Identity": As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

"Low Molecular Weight Polymer": As used herein, the term "low molecular weight polymer" refers to polymers and/or polymer solutions, such as silk, included of polymers (e.g., protein polymers) having molecular weights within the range of about 20 kDa-about 400 kDa. In some embodiments, low molecular weight polymers (e.g., protein polymers) have molecular weights within a range between a lower bound (e.g., about 20 kDa, about 30 kDa, about 40 kDa, about 50 kDa, about 60 kDa, or more) and an upper bound (e.g., about 400 kDa, about 375 kDa, about 350 kDa, about 325 kDa, about 300 kDa, or less). In some embodiments, low molecular weight polymers (e.g., protein polymers such as silk) are substantially free of, polymers having a molecular weight above about 400 kD. In some embodiments, the highest molecular weight polymers in provided hydrogels are less than about 300-about 400 kD (e.g., less than about 400 kD, less than about 375 kD, less than about 350 kD, less than about 325 kD, less than about 300 kD, etc). In some embodiments, a low molecular weight polymer and/or polymer solution can include a population of polymer fragments having a range of molecular weights, characterized in that: no more than 15% of the total moles of polymer fragments in the population has a molecular weight exceeding 200 kDa, and at least 50% of the total moles of the silk fibroin fragments in the population has a molecular weight within a specified range, where the specified range is between about 3.5 kDa and about 120 kDa or between about 5 kDa and about 125 kDa.

"Marker": A marker, as used herein, refers to an entity or moiety whose presence or level is a characteristic of a particular state or event. In some embodiments, presence or level of a particular marker may be characteristic of presence or stage of a disease, disorder, or condition. To give but one example, in some embodiments, the term refers to a gene expression product that is characteristic of a particular tumor, tumor subclass, stage of tumor, etc. Alternatively or additionally, in some embodiments, a presence or level of a particular marker correlates with activity (or activity level) of a particular signaling pathway, for example that may be characteristic of a particular class of tumors. The statistical significance of the presence or absence of a marker may vary depending upon the particular marker. In some embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker). Conversely, markers with a high degree of sensitivity may be less specific that those with lower sensitivity. According to the present disclosure a useful marker need not distinguish tumors of a particular subclass with 100% accuracy.

"Modulator": The term "modulator" is used to refer to an entity whose presence or level in a system in which an activity of interest is observed correlates with a change in level and/or nature of that activity as compared with that observed under otherwise comparable conditions when the modulator is absent. In some embodiments, a modulator is an activator, in that activity is increased in its presence as compared with that observed under otherwise comparable conditions when the modulator is absent. In some embodiments, a modulator is an antagonist or inhibitor, in that activity is reduced in its presence as compared with otherwise comparable conditions when the modulator is absent. In some embodiments, a modulator interacts directly with a target entity whose activity is of interest. In some embodiments, a modulator interacts indirectly (i.e., directly with an intermediate agent that interacts with the target entity) with a target entity whose activity is of interest. In some embodiments, a modulator affects level of a target entity of interest; alternatively or additionally, in some embodiments, a modulator affects activity of a target entity of interest without affecting level of the target entity. In some embodiments, a modulator affects both level and activity of a target entity of interest, so that an observed difference in activity is not entirely explained by or commensurate with an observed difference in level.

"Nanoparticle": As used herein, the term "nanoparticle" refers to a particle having a diameter of less than 1000 nanometers (nm). In some embodiments, a nanoparticle has a diameter of less than 300 nm, as defined by the National Science Foundation. In some embodiments, a nanoparticle has a diameter of less than 100 nm as defined by the National Institutes of Health. In some embodiments, nanoparticles are micelles in that they include an enclosed compartment, separated from the bulk solution by a micellar membrane, typically comprised of amphiphilic entities which surround and enclose a space or compartment (e.g., to define a lumen). In some embodiments, a micellar membrane is included of at least one polymer, such as for example a biocompatible and/or biodegradable polymer.

"Nanoparticle composition": As used herein, the term "nanoparticle composition" refers to a composition that contains at least one nanoparticle and at least one additional agent or ingredient. In some embodiments, a nanoparticle composition contains a substantially uniform collection of nanoparticles as described herein.

"Nucleic acid": As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present disclosure. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can include nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment includes at least 3, 4, 5, 6, 7, 8, 9, 10, or more residues. In some embodiments, a nucleic acid is or includes natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present disclosure is specifically directed to "unmodified nucleic acids," meaning nucleic acids (e.g., polynucleotides and residues, including nucleotides and/or nucleosides) that have not been chemically modified in order to facilitate or achieve delivery.

"Pharmaceutical composition": As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

"Physiological conditions": The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 6.8 to about 8.0 and a temperature range of about 20-40 degrees Celsius, about 25-40° C., about 30-40° C., about 35-40° C., about 37° C., atmospheric pressure of about 1. In some embodiments, physiological conditions utilize or include an aqueous environment (e.g., water, saline, Ringers solution, or other buffered solution); in some such embodiments, the aqueous environment is or includes a phosphate buffered solution (e.g., phosphate-buffered saline).

"Polypeptide": The term "polypeptide", as used herein, generally has its art-recognized meaning of a polymer of at least three amino acids, linked to one another by peptide bonds. In some embodiments, the term is used to refer to specific functional classes of polypeptides. For each such class, the present specification provides several examples of amino acid sequences of known exemplary polypeptides within the class; in some embodiments, such known polypeptides are reference polypeptides for the class. In such embodiments, the term "polypeptide" refers to any member of the class that shows significant sequence homology or identity with a relevant reference polypeptide. In many embodiments, such member also shares significant activity with the reference polypeptide. Alternatively or additionally, in many embodiments, such member also shares a particular characteristic sequence element with the reference polypeptide (and/or with other polypeptides within the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (i.e., a conserved region that may in some embodiments may be or include a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may include or consist of a fragment of a parent polypeptide. In some embodiments, a useful polypeptide as may include or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide. In some embodiments, a polypeptide may include natural amino acids, non-natural amino acids, or both. In some embodiments, a polypeptide may include only natural amino acids or only non-natural amino acids. In some embodiments, a polypeptide may include D-amino acids, L-amino acids, or both. In some embodiments, a polypeptide may include only D-amino acids. In some embodiments, a polypeptide may include only L-amino acids. In some embodiments, a polypeptide may include one or more pendant groups, e.g., modifying or attached to one or more amino acid side chains, and/or at the polypeptide's N-terminus, the polypeptide's C-terminus, or both. In some embodiments, a polypeptide may be cyclic. In some embodiments, a polypeptide is not cyclic. In some embodiments, a polypeptide is linear.

"Polysaccharide": The term "polysaccharide" refers to a polymer of sugars. Typically, a polysaccharide includes at least three sugars. In some embodiments, a polypeptide includes natural sugars (e.g., glucose, fructose, galactose, mannose, arabinose, ribose, and xylose); alternatively or additionally, in some embodiments, a polypeptide includes one or more non-natural amino acids (e.g. modified sugars such as 2'-fluororibose, 2'-deoxyribose, and hexose).

"Porosity": The term "porosity" as used herein, refers to a measure of void spaces in a material and is a fraction of volume of voids over the total volume, as a percentage between 0 and 100%. A determination of a porosity is known to a skilled artisan using standardized techniques, for example mercury porosimetry and gas adsorption (e.g., nitrogen adsorption).

"Protein": As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may include natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

"Reference": The term "reference" is often used herein to describe a standard or control agent, individual, population, sample, sequence or value against which an agent, individual, population, sample, sequence or value of interest is compared. In some embodiments, a reference agent, individual, population, sample, sequence or value is tested and/or determined substantially simultaneously with the testing or determination of the agent, individual, population, sample, sequence or value of interest. In some embodiments, a reference agent, individual, population, sample, sequence or value is a historical reference, optionally embodied in a tangible medium. Typically, as would be understood by those skilled in the art, a reference agent, individual, population, sample, sequence or value is determined or characterized under conditions comparable to those utilized to determine or characterize the agent, individual, population, sample, sequence or value of interest.

"Small molecule": As used herein, the term "small molecule" is used to refer to molecules, whether naturally-occurring or artificially created (e.g., via chemical synthesis), having a relatively low molecular weight and being an organic and/or inorganic compound. Typically, a "small molecule" is monomeric and have a molecular weight of less than about 1500 g/mol. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not a protein or polypeptide (e.g., is not an oligopeptide or peptide). In some embodiments, a small molecule is not a polynucleotide (e.g., is not an oligonucleotide). In some embodiments, a small molecule is not a polysaccharide. In some embodiments, a small molecule does not include a polysaccharide (e.g., is not a glycoprotein, proteoglycan, glycolipid, etc.). In some embodiments, a small molecule is not a lipid. In some embodiments, a small molecule is a modulating agent. In some embodiments, a small molecule is biologically active. In some embodiments, a small molecule is detectable (e.g., includes at least one detectable moiety). In some embodiments, a small molecule is a therapeutic. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§ 330.5, 331 through 361, and 440 through 460; drugs for veterinary use listed by the FDA under 21 C.F.R. §§ 500 through 589, incorporated herein by reference, are all considered acceptable for use in accordance with the present application.

"Solution": As used herein, the term "solution" broadly refers to a homogeneous mixture composed of one phase. Typically, a solution includes a solute or solutes dissolved in a solvent or solvents. It is characterized in that the properties of the mixture (such as concentration, temperature, and density) can be uniformly distributed through the volume. In the context of the present application, therefore, a "silk fibroin solution" refers to silk fibroin protein in a soluble form, dissolved in a solvent, such as water. In some embodiments, silk fibroin solutions may be prepared from a solid-state silk fibroin material (i.e., silk matrices), such as silk films and other scaffolds. Typically, a solid-state silk fibroin material is reconstituted with an aqueous solution, such as water and a buffer, into a silk fibroin solution. It should be noted that liquid mixtures that are not homogeneous, e.g., colloids, suspensions, emulsions, are not considered solutions.

"Stable": The term "stable," when applied to compositions herein, means that the compositions maintain one or more aspects of their physical structure and/or activity over a period of time under a designated set of conditions. In some embodiments, the period of time is at least about one hour; in some embodiments, the period of time is about 5 hours, about 10 hours, about one (1) day, about one (1) week, about two (2) weeks, about one (1) month, about two (2) months, about three (3) months, about four (4) months, about five (5) months, about six (6) months, about eight (8) months, about ten (10) months, about twelve (12) months, about twenty-four (24) months, about thirty-six (36) months, or longer. In some embodiments, the period of time is within the range of about one (1) day to about twenty-four (24) months, about two (2) weeks to about twelve (12) months, about two (2) months to about five (5) months, etc. In some embodiments, the designated conditions are ambient conditions (e.g., at room temperature and ambient pressure). In some embodiments, the designated conditions are physiologic conditions (e.g., in vivo or at about 37° C. for example in serum or in phosphate buffered saline). In some embodiments, the designated conditions are under cold storage (e.g., at or below about 4° C., −20° C., or −70° C.). In some embodiments, the designated conditions are in the dark.

"Substantially": As used herein, the term "substantially", and grammatic equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

"Sustained release": The term "sustained release" is used herein in accordance with its art-understood meaning of release that occurs over an extended period of time. The extended period of time can be at least about 3 days, about 5 days, about 7 days, about 10 days, about 15 days, about 30 days, about 1 month, about 2 months, about 3 months, about 6 months, or even about 1 year. In some embodiments, sustained release is substantially burst-free. In some embodiments, sustained release involves steady release over the extended period of time, so that the rate of release does not vary over the extended period of time more than about 5%, about 10%, about 15%, about 20%, about 30%, about 40% or about 50%. In some embodiments, sustained release involves release with first-order kinetics. In some embodiments, sustained release involves an initial burst, followed by a period of steady release. In some embodiments, sustained release does not involve an initial burst. In some embodiments, sustained release is substantially burst-free release.

"Therapeutic agent": As used herein, the phrase "therapeutic agent" refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

"Therapeutically effective amount": As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." To give but one example, a refractory subject may have a low bioavailability such that clinical efficacy is not obtainable. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc). Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

"Treating": As used herein, the term "treating" refers to partially or completely alleviating, ameliorating, relieving, inhibiting, preventing (for at least a period of time), delaying onset of, reducing severity of, reducing frequency of and/or reducing incidence of one or more symptoms or features of a particular disease, disorder, and/or condition. In some embodiments, treatment may be administered to a subject who does not exhibit symptoms, signs, or characteristics of a disease and/or exhibits only early symptoms, signs, and/or characteristics of the disease, for example for the purpose of decreasing the risk of developing pathology associated with the disease. In some embodiments, treatment may be administered after development of one or more symptoms, signs, and/or characteristics of the disease.

"Variant": As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs double, E vs Z, etc.) within the core, a polypeptide may have a characteristic sequence element included of a plurality of amino acids having designated positions relative to one another in linear or three-dimensional space and/or contributing to a particular biological function, a nucleic acid may have a characteristic sequence element included of a plurality of nucleotide residues having designated positions relative to on another in linear or three-dimensional space. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

DETAILED DESCRIPTION OF CERTAIN EMBODIMENTS

Worldwide there are millions of people who suffer from conditions that affect their ability to see clearly. Nearsightedness (myopia), far-sightedness (hyperopia), corneal injury, and corneal ectatic diseases can significantly deteriorate visual acuity. For many, glasses or contact lenses can be used to restore eyesight, but the rise of surgical procedures to correct vision such as laser-assisted in situ keratomileusis (LASIK) indicates that corrective lenses are inadequate. Though typically well-tolerated, side effects from LASIK procedures can be permanent and debilitating. (See A. Yildirim, H. Cakir, N. Kara, H. Uslu, B. Gurler, E. B. Ozgurhan, H. N. Colak. Journal Of Cataract and Refractive Surgery, pages 1-6 (2014) hereby incorporated by reference in its entirety herein). Since LASIK involves removing native corneal tissue, it cannot be performed safely on patients whose corneas are already thinned due to genetics or disease.

Among other things, the present disclosure provides silk fibroin-based hydrogels and methods of preparing and using such silk fibroin-based hydrogels. Various embodiments according to the present disclosure are described in detail herein. The present disclosure describes silk fibroin-based hydrogels and their use in various application, including, for example: biomaterials, biomedical, biosensing, drug delivery, electronics, optics, optogenetics, photonics, regenerative medicine, tissue engineering applications, tissue regeneration, utility for transparent tissues, superior adhesion, degradation resistance, tunable degradation, and/or controlled release applications. In particular, the present disclosure describes silk fibroin-based hydrogels for use as an ocular prosthesis.

For biomedical applications, one of the material formats that can be used is a hydrogel, which allows for ease of cell infiltration, high water contents, swellability, and/or the ability to control the release of drugs and other therapeutic agents dispersed therein. In biomedical applications, hydrogels have been used as bioactive polymers. The high water content and mechanical response of hydrogels can them desirable and suitable for both cell engineering and tissue restoration applications.

Traditional hydrogels are typically made from synthetic and natural polymers, for example, polyesters, polyurethanes, polyethers, elastin, resilin. Synthetic polymers have also been developed that exhibit high resilience and recovery from both applied tensile and compressive forces. Poly(glycerol sebacate) (PGS) for example has shown utility as a scaffold for engineering vascular, cardiac, and nerve tissues. Additionally, synthetic bioelastomers based on polyurethanes, including for examples variants of poly(ethylene glycol), poly($\varepsilon$-caprolactone), and poly(vinyl alcohol), modified with degradable segments have also been developed and used for soft tissue, bone, and myocardial repairs.

Traditional hydrogels cannot offer a combination of all of these characteristics. For example, previously developed hydrogel technologies typically lack certain of the mechanical properties described for hydrogels herein, and/or lack the ability to specifically tune such properties, e.g., via production methodologies. Alternatively or additionally, previously developed hydrogel technologies typically lack certain of the favorable degradation mechanics provided by hydrogels described herein and/or lack the ability to specifically tune such properties. Still further, in many cases, traditional hydrogels fail to display certain degradation properties described for hydrogels provided herein; rapid degradation of such previously-developed hydrogels often limits their use to short term scaffolding. Yet further, in many cases, traditional hydrogel technologies require organic solvents during processing, which can result in toxicity, can interfere with cell or protein encapsulation (and particularly with maintenance of structural and/or functional integrity of encapsulated entities), and cannot resist long term strains when incorporated in vivo.

In many cases, traditional hydrogels form through physical entanglements and hydrogen bonding between hydrophobic domains, resulting in $\beta$-sheet formation. $\beta$-sheet crystals have been shown to provide structure, strength, and long term stability of hydrogels. But, $\beta$-sheet crystals also display brittle behavior, as the crystals prevent long range displacements. Hydrogel technologies described herein provide sophisticated control, selected ion, and/or balance of such properties.

Solubilized silk fibroin has traditionally allowed the creation of unique three-dimensional morphologies and materials for applications that range beyond the traditional textile-based applications. Silk fibroin that has been under steady investigation for decades due to its numerous attractive characteristics: biocompatibility, cytocompatibility, mechanical strength, ability to stabilize labile compounds, and biodegredability. (See H. Tao, D. L. Kaplan, F. G. Omenetto, 24 Advanced Materials 21, 2824 (2012)).

Silk fibroin is used as a sustainable material for biomedical, optics, photonics and electronics applications has been predicated on the numerous material formats, for example, fibers, foams, particles, films, hydrogels, in which silk fibroin can be processed after regeneration in aqueous solution. (See H. Tao, 24 Adv. Mater., 2824-37 (2012) hereby incorporated by reference in its entirety herein). Additionally, silk fibroin materials can be engineered with tunable morphological, physical, mechanical and biological properties by fine regulation of molecular weight at the point of protein extraction from silk fibers during the removal of sericin and by controlling the degree of crystallinity through exposure to heat, water vapor or polar solvents. (See H. Tao, 24 Adv. Mater., 2824-37 (2012) and F. G. Omenetto, 329 Science, 528-531 (2010) herein incorporated by reference in their entirety).

Hydrogels have been previously formed from silk fibroin, for example, by covalent crosslinking, sonication, vortexing, electrical current, introduction of ions, the addition of PEG and/or poloxamer solutions. Silk fibroin hydrogels have been proposed as substrates for the engineering, modeling and regeneration of soft tissues, ranging from nerves to cartilage. (See P. H. G. Chao, 95 J. Biomed. Mater., Res. B. Appl. Biomater., 84-90 (2010) and A. M. Hopkins, 23 Adv. Funct. Mater., 5140-5149 (2013) hereby incorporated by reference in their entirety). There is in fact a need for soft biomaterials that match the physical and mechanical properties of human tissues by mimicking the hydrated nature of the extracellular space. (See J. L. Drury, 24 Biomaterials, 4337-4351 (2003), N. A. Peppas, 18 Adv. Mater., 1345-1360 (2006) hereby incorporated by reference in its entirety herein, and J. Zhu, 8 Expert Rev. Med. Devices, 607-26 (2011) herein incorporated by reference in their entirety). In addition, silk fibroin hydrogels can be easily modified to provide appropriate morphological, biochemical and mechanical cues and can be functionalized with stabilized heat-labile compounds. (See N. Guziewicz, 32 Biomaterials, 2642-50 (2011) hereby incorporated by reference in its entirety herein).

Silk fibroin sol-gel transition occurs through inter-molecular and intra-molecular interactions (mainly formation of hydrogen bonds and hydrophobic interactions) among protein chains, which fold from amorphous to thermodynamically stable $\beta$-sheets, driven by exposure of silk fibroin solutions to shear forces, electric fields, pH near or below the isoelectric point (pI=3.8-3.9), polar solvents, heat and water removal. (See U. J. Kim, 5 Biomacromolecules, 786-92 (2004) and S. Nagarkar, 12 Phys. Chem. Chem. Phys., 3834-44 (2010) herein incorporated by reference in their entirety). The soft-micelle assembly process is also regulated by the strong amphiphilic (hydrophobic and hydrophilic domains) nature of the protein, where short hydrophilic (amorphous) spacers intervene between large hydrophobic (crystallizable) blocks and play a critical role in preventing premature $\beta$-sheet formation and in modulating water solubility. (See H. J. Jin, 424 Nature, 1057-61 (2003) herein incorporated by reference in its entirety).

Development of inter-molecular bonds results in aggregation of silk fibroin micelles into interconnected micron-sized particles with progressive loss of transparency of the silk fibroin solution, ultimately becoming a white hydrogel due to light scattering (FIG. 11). Despite numerous applications of silk fibroin-based hydrogels in biomedical engineering, the lack of transparency has been of hindrance to fully capitalize on this material format. (See M. Choi, 7 Nat. Photonics, 987-994 (2013) herein incorporated by reference in its entirety). For example, biological entities (e.g. cells), light sensitive molecules (e.g. fluorescent, bioluminescent, photoactive macromolecules) and optogenetic tools can be incorporated into hydrogels for sensing and diagnostic applications, to generate biomimetic biological systems or to build optical interfaces with living tissues.

Silk fibroin is also attractive as an optical material due to its near perfect transparency to visible light and has been used to make a wide variety of optical elements including lenses, phase masks, diffraction gratings (see J. P. Modina, J. J. Amsden, D. Lin, L. D. Negro, D. L. Kaplan, 22 Adv. Mater. 4596 (2010) hereby incorporated by reference in its entirety herein), lasers (see S. Toffanin, S. Kim, S. Cavallini, M. Natali, V. Benfenati, J. J. Amsden, D. L. Kaplan, R. Zamboni, F. G. Omenetto, 101 Appl. Phys. Lett., 091110 (2012) hereby incorporated by reference in its entirety herein; see also Y. Choi, H. Jeon, S. Kim, 15 Lab Chip, 642 (2015) hereby incorporated by reference in its entirety herein), photonic crystals (see S. Kim, A. N. Mitropoulos, J. D. Spitzberg, H. Tao, D. L. Kaplan, F. G. Omenetto, 6 Nat. Photonics 818 (2012) hereby incorporated by reference in its entirety herein), and waveguides (see S. T. Parker, P. Domachuk, J. J. Amsden, J. Bressner, J. A. Lewis, D. L. Kaplan, F. G. Omenetto, 21 Adv. Mater., 2411 (2009) hereby incorporated by reference in its entirety herein; see also M. B. Applegate, G. Perotto, D. L. Kaplan, F. G. Omenetto, 6 Biomed. Opt. Express, 4221 (2015) hereby incorporated by reference in its entirety herein). This combination of properties makes silk fibroin a promising material for use in ocular prostheses.

For optics and photonics applications, the film format for silk has generated interest due to transparency, robust mechanical properties and preservation of heat-labile sensing molecules encapsulated within the protein, allowing for the fabrication of optic and photonic devices with unprecedented features that can be interfaced with biology. (See F. G. Omenetto, 2 Nat. Photonics, 641-643 (2008) herein incorporated by referenced in its entirety. Conversely, other commonly used material formats of silk fibroin, such as foams and hydrogels are characterized by high optical loss due to internal light scattering. (See U. J. Kim, 5 Biomacromolecules, 786-92 (2004), S. Nagarkar, 12 Phys. Chem. Chem. Phys., 3834-44 (2010), and D. N. Rockwood, 6 Nat. Protoc., 1612-31 (2011) herein incorporated by reference in their entirety). Transparency is also the main characteristic of cornea tissue where silk fibroin has shown potential as scaffolding material for cornea replacements. (See T. Chirila, 561-565 Materials Science Forum, 1549-1552 (2007), T. V. Chirila, 14 Tissue Eng Part A, 1203-11 (2008), K. Higa, 27 Cornea, Suppl 1, S41-7 (2008), E. S. Gil, 10 Macromol. Biosci., 664-73 (2010), J. Wu, 35 Biomaterials, 3744-55 (2014), B. D. Lawrence, 8 Acta Biomater., 3732-3743 (2012), E. S. Gil, 31 Biomaterials, 8953-63 (2010), B. D. Lawrence, 30 Biomaterials, 1299-308 (2009) herein incorporated by reference in their entirety).

Provided silk fibroin-based hydrogels are characterized by unique features that provide advantages over existing hydrogels. Silk fibroin-based hydrogels of the present disclosure exhibit optical clarity and/or optically transparent in the visible spectrum.

In some embodiments, the present disclosure provides silk fibroin-based hydrogels suited for implantation in or on tissues, such as corneal tissue. In some embodiments, the present disclosure provides methods of making and using provided silk fibroin-based hydrogels.

Silk fibroin-based hydrogels provided herein exhibit superior adhesion to tissues. In particular, provided silk fibroin-based hydrogels show superior adhesion, for example, when applied to corneal tissue. In some embodiments, riboflavin and illumination with blue light are used to crosslink liquid silk fibroin solution resulting in a transparent, elastic hydrogel, that forms a tight association with native corneal collagen. In some embodiments, the result is a layer of silk overlaying corneal tissue that is useful to improve vision.

In some embodiments, these methods produce silk fibroin hydrogels with highly tunable final material properties. In some embodiments, silk fibroin-based hydrogels of the present disclosure are adaptable for use both with a wide array of tissue types and in different applications. In some embodiments, silk fibroin-based hydrogels of the present disclosure are tunable so that mechanical properties may be tailored, for example, to be used as an ocular prosthesis.

Provided silk fibroin-based hydrogels are non-toxic and biodegradable. Provided silk fibroin-based hydrogels are capable of being formed, molded, shaped, and/or machined into desired structures. In some embodiments, these methods produce silk fibroin hydrogels as described herein that are useful as a corneal prosthesis to improve visual acuity without the risks associated with LASIK.

Provided silk fibroin-based hydrogels have widely tunable mechanical properties. Provided silk fibroin-based hydrogels are characterized by tuning their mechanical properties so that they are capable of including additives, agents, and/or functional moieties (e.g. cells). In some embodiments, including additives, agents, and/or functional moieties are beneficial for prevention or treatment of a condition, disease, or disorder.

In medicine, light-based imaging techniques have been used for centuries. However, by comparison, the direct use of light for therapeutic purposes is rare. Corneal collagen crosslinking (CXL) is one such light-based therapy that uses riboflavin as a photosensitizer to crosslink corneal collagen. This technique is currently being used to treat corneal ectatic diseases which are characterized by a progressive thinning of the cornea. (See G. Wollensak, E. Spoerl, T. Seiler, 135 American Journal of Ophthalmology 5, 620 (2003)). Though CXL can slow the progression of these diseases, it does little to restore visual acuity.

Previous work has shown ruthenium capable of photocrosslinking silk, (see J. L. Whittaker, N. R. Choudhury, N. K. Dutta, A. Zannettino, 2 Journal of Materials Chemistry B 37, 6259 (2014) hereby incorporated by reference in its entirety herein), however, under certain conditions ruthenium can be highly toxic and is being investigated as a potential chemotherapeutic for cancer. (See H. A. Wee, P. J. Dyson, 20 European Journal of Inorganic Chemistry, 4003 (2006) hereby incorporated by reference in its entirety herein). For in vivo use a non-toxic photoinitiator is desirable.

Riboflavin absorbs light strongly between 330 and 470 nm with peak absorbance in this range occurring at 350 and 450 nm, and a fluorescence emission peak at 533 nm. (See J. M. Dixon, M. Taniguchi, J. S. Lindsey, 81 Photochem. Photobiol., 212 (2007) hereby incorporated by reference in its entirety herein). Riboflavin photocrosslinking is quite nonspecific and has been shown to occur in many materials including collagen, (see S. Ibusuki, G. J. Halbesma, M. a. Randolph, R. W. Redmond, I. E. Kochevar, T. J. Gill. 13 Tissue Engineering 8, 1995 (2007) hereby incorporated by reference in its entirety herein; see also E. Masurovsky, E. Peterson, 76 Experimental Cell Research 2, 447 (1973) hereby incorporated by reference in its entirety herein), alginate, (see S.-H. Kim, C.-C. Chu, 91 Journal of Biomedical Materials Research Part B, Applied Biomaterials 1, 390 (2009) hereby incorporated by reference in its entirety herein), and poly(ethylene glycol) (see A. K. Nguyen, S. D. Gittard, A. Koroleva, S. Schlie, A. Gaidukeviciute, B. N. Chichkov, R. J. Narayan, 8 Regenerative Medicine 6, 725 (2013) hereby incorporated by reference in its entirety herein).

The present disclosure provides technologies for forming silk fibroin-based hydrogels. In some embodiments, methods can employ all aqueous processing, commonly available reagents, and do not need to rely on expensive or complicated equipment (power supply, sonicator, vortexer, etc.) or volatile chemicals to induce gelation.

The present disclosure appreciates that riboflavin is an attractive photoinitiator for biomedical applications. Among other things, the present disclosure appreciates that riboflavin is found naturally in tissues, and also is able to crosslink molecules via exposure to harmless visible light rather than potentially damaging ultraviolet radiation. While not wishing to be bound to any particular theory, in some embodiments, a gelation mechanism of silk-riboflavin is photocrosslinking.

In some embodiments, flavin-mononucleotide (FMN), a water soluble variant of riboflavin, is used as a photoinitiator to catalyze transition of a liquid silk solution to a highly elastic hydrogel in the presence of light.

In some embodiments, the present disclosure encompasses an ability to generate high resolution patterns of silk using photolithography.

In some embodiments, silk hydrogels adhere to de-epithelialized cornea (e.g., of enucleated porcine eyes).

In some embodiments, the present disclosure teaches that combining high-resolution patterning with corneal adhesion could feasibly alter optical thickness of the cornea with high spatial resolution to improve visual acuity.

In some embodiments, technologies provided herein (e.g., silk hydrogel production using a flavin compound) are useful in people suffering from myopia, hyperopia, and corneal ectatic disorders; in some embodiments, provided technologies can reduce or eliminate reliance on and/or performance of procedures such as LASIK (see, e.g., Yildirim et al. Journal Of Cataract and Refractive Surgery, pages 1-6 (2014) hereby incorporated by reference in its entirety herein), and therefore can avoid risks attendant with such procedure(s). In some embodiments, provided technologies may be utilized in combination with one or more other treatments for the relevant disease, disorder or condition; in some such embodiments, such other treatments do not include LASIK.

In some embodiments, a flavin, such as riboflavin, is used to photocrosslink silk fibroin. In some embodiments, light and riboflavin initiate crosslinking.

Hydrogels

In some embodiments, hydrogels of the present disclosure are polymer hydrogels (i.e., include or consist of polymers). In some embodiments, such polymers are or include proteins.

In some embodiments, a polymer is natural or synthetic. In some embodiments, a polymer includes one or more polypeptides or proteins. In some embodiments, degradable polymers known in the art include, for example, certain polyesters, polyanhydrides, polycaptolactone, polyorthoesters, polyphosphazenes, polyphosphoesters, certain polyhydroxyacids, polypropylfumerates, polycaprolactones, polyamides, poly(amino acids), polyacetals, polyethers, biodegradable polycyanoacrylates, biodegradable polyurethanes, poly(glycerol sebacates), elastomeric poly(glycerol sebacates polysaccharides), polypyrrole, polyanilines, polythiophene, polystyrene, polyesters, polyureas, poly(ethylene vinyl acetate), polypropylene, polymethacrylate, polyethylene, polycarbonates, poly(ethylene oxide), polysaccharides, co-polymers, and combinations thereof. For example, specific biodegradable polymers that may be used include but are not limited to polylysine (e.g., poly(L-lysine) ("PLL")), poly(lactic acid) ("PLA"), poly(glycolic acid) ("PGA"), polylactic acid/poly(glycolide-colactide) copolymer ("PLGA"), poly(caprolactone) ("PCL"), poly(lactide-co-glycolide) ("PLG"), poly(lactide-co-caprolactone) ("PLC"), poly(glycolide-co-caprolactone) ("PGC"), poly(styrene sulfonate) ("SPS"), poly(acrylic acid) ("PAA"), linear poly (ethylene imine) ("LPEI"), poly(diallyldimethyl ammonium chloride) ("PDAC"), and poly(allylamine hydrochloride) ("PAH"). Another exemplary degradable polymer is poly (beta-amino esters), which may be suitable for use in accordance with the present application. Those skilled in the art will recognize that this is an exemplary, not comprehensive, list of polymers.

In some embodiments, a polymer is includes amino acid phenolic side chains.

In some embodiments, protein polymers of are selected from the group consisting of agarose, alginate, cellulose, chitin, chitosan, collagen, elastin, gelatin, hyaluronic acid, polydimethylsiloxane, poly(ethylene glycol), polyhydroxyalkanoates, poly(lactide-co-glycolide), pullan, resilin, silk, starch, or combinations thereof.

In some embodiments, a protein polymer is or includes silk fibroin. In some embodiments, a protein polymer solution is a silk fibroin solution. In some embodiments, silk fibroin-based hydrogels are or include silk fibroin and/or silk fibroin fragments. In some embodiments, such as silk, amino acid phenolic side chains are tyrosine.

Silks

In some embodiments, a polymer is silk. Silk is a natural protein fiber produced in a specialized gland of certain organisms. Silk production in organisms is especially common in the Hymenoptera (bees, wasps, and ants), and is sometimes used in nest construction. Other types of arthropod also produce silk, most notably various arachnids such as spiders (e.g., spider silk). Silk fibers generated by insects and spiders represent the strongest natural fibers known and rival even synthetic high performance fibers.

Silk has been a highly desired and widely used textile since its first appearance in ancient China (see Elisseeff, "The Silk Roads: Highways of Culture and Commerce," Berghahn Books/UNESCO, New York (2000) hereby incorporated by reference in its entirety herein; see also Vainker, "Chinese Silk: A Cultural History," Rutgers University Press, Piscataway, N.J. (2004) hereby incorporated by reference in its entirety herein). Glossy and smooth, silk is favored by not only fashion designers but also tissue engineers because it is mechanically tough but degrades harmlessly inside the body, offering new opportunities as a highly robust and biocompatible material substrate (see Altman et al., Biomaterials, 24: 401 (2003) hereby incorporated by reference in its entirety herein; see also Sashina et al., Russ. J. Appl. Chem., 79: 869 (2006) hereby incorporated by reference in its entirety herein).

Silk is naturally produced by various species, including, without limitation: *Antheraea mylitta; Antheraea pernyi; Antheraea yamamai; Galleria mellonella; Bombyx mori; Bombyx mandarina; Galleria mellonella; Nephila clavipes; Nephila senegalensis; Gasteracantha mammosa; Argiope aurantia; Araneus diadematus; Latrodectus geometricus; Araneus bicentenarius; Tetragnatha versicolor; Araneus ventricosus; Dolomedes tenebrosus; Euagrus chisoseus; Plectreurys tristis; Argiope trifasciata*; and *Nephila madagascariensis.*

In general, silk for use in accordance with the present disclosure may be produced by any such organism, or may be prepared through an artificial process, for example, involving genetic engineering of cells or organisms to produce a silk protein and/or chemical synthesis. In some embodiments of the present disclosure, silk is produced by the silkworm, *Bombyx mori*.

As is known in the art, silks are modular in design, with large internal repeats flanked by shorter (~100 amino acid) terminal domains (N and C termini). Naturally-occurring silks have high molecular weight (200 to 350 kDa or higher) with transcripts of 10,000 base pairs and higher and >3000 amino acids (reviewed in Omenatto and Kaplan (2010) Science 329: 528-531). The larger modular domains are interrupted with relatively short spacers with hydrophobic charge groups in the case of silkworm silk. N- and C-termini are involved in the assembly and processing of silks, including pH control of assembly. The N- and C-termini are highly conserved, in spite of their relatively small size compared with the internal modules.

Table 1, below, provides an exemplary list of silk-producing species and silk proteins:

TABLE 1

An exemplary list of silk-producing species and silk proteins (adopted from Bini et al. (2003), J. Mol. Biol. 335(1): 27-40).

| Accession | Species | Producing gland | Protein |
|---|---|---|---|
| A. Silkworms | | | |
| AAN28165 | *Antheraea mylitta* | Salivary | Fibroin |
| AAC32606 | *Antheraea pernyi* | Salivary | Fibroin |
| AAK83145 | *Antheraea yamamai* | Salivary | Fibroin |
| AAG10393 | *Galleria mellonella* | Salivary | Heavy-chain fibroin (N-terminal) |
| AAG10394 | *Galleria mellonella* | Salivary | Heavy-chain fibroin (C-terminal) |
| P05790 | *Bombyx mori* | Salivary | Fibroin heavy chain precursor, Fib-H, H-fibroin |
| CAA27612 | *Bombyx mandarina* | Salivary | Fibroin |
| Q26427 | *Galleria mellonella* | Salivary | Fibroin light chain precursor, Fib-L, L-fibroin, PG-1 |
| P21828 | *Bombyx mori* | Salivary | Fibroin light chain precursor, Fib-L, L-fibroin |
| B. Spiders | | | |
| P19837 | *Nephila clavipes* | Major ampullate | Spidroin 1, dragline silk fibroin 1 |
| P46804 | *Nephila clavipes* | Major ampullate | Spidroin 2, dragline silk fibroin 2 |
| AAK30609 | *Nephila senegalensis* | Major ampullate | Spidroin 2 |
| AAK30601 | *Gasteracantha mammosa* | Major ampullate | Spidroin 2 |
| AAK30592 | *Argiope aurantia* | Major ampullate | Spidroin 2 |
| AAC47011 | *Araneus diadematus* | Major ampullate | Fibroin-4, ADF-4 |
| AAK30604 | *Latrodectus geometricus* | Major ampullate | Spidroin 2 |
| AAC04503 | *Araneus bicentenarius* | Major ampullate | Spidroin 2 |
| AAK30615 | *Tetragnatha versicolor* | Major ampullate | Spidroin 1 |
| AAN85280 | *Araneus ventricosus* | Major ampullate | Dragline silk protein-1 |
| AAN85281 | *Araneus ventricosus* | Major ampullate | Dragline silk protein-2 |
| AAC14589 | *Nephila clavipes* | Minor ampullate | MiSp1 silk protein |
| AAK30598 | *Dolomedes tenebrosus* | Ampullate | Fibroin 1 |
| AAK30599 | *Dolomedes tenebrosus* | Ampullate | Fibroin 2 |
| AAK30600 | *Euagrus chisoseus* | Combined | Fibroin 1 |
| AAK30610 | *Plectreurys tristis* | Larger ampule-shaped | Fibroin 1 |
| AAK30611 | *Plectreurys tristis* | Larger ampule-shaped | Fibroin 2 |
| AAK30612 | *Plectreurys tristis* | Larger ampule-shaped | Fibroin 3 |
| AAK30613 | *Plectreurys tristis* | Larger ampule-shaped | Fibroin 4 |
| AAK30593 | *Argiope trifasciata* | Flagelliform | Silk protein |
| AAF36091 | *Nephila madagascariensis* | Flagelliform | Fibroin, silk protein (N-terminal) |
| AAF36092 | *Nephila madagascariensis* | Flagelliform | Silk protein (C-terminal) |
| AAC38846 | *Nephila clavipes* | Flagelliform | Fibroin, silk protein (N-terminal) |
| AAC38847 | *Nephila clavipes* | Flagelliform | Silk protein C-terminal) |

Silk Fibroin

Fibroin is a type of structural protein produced by certain spider and insect species that produce silk. Cocoon silk produced by the silkworm, *Bombyx mori*, is of particular interest because it offers low-cost, bulk-scale production suitable for a number of commercial applications, such as textile.

Silkworm cocoon silk contains two structural proteins, the fibroin heavy chain (~350 kDa) and the fibroin light chain (~25 kDa), which are associated with a family of non-structural proteins termed sericin, which glue the fibroin brings together in forming the cocoon. The heavy and light chains of fibroin are linked by a disulfide bond at the C-terminus of the two subunits (see Takei, F., Kikuchi, Y., Kikuchi, A., Mizuno, S. and Shimura, K. (1987) 105 J. Cell Biol., 175-180; see also Tanaka, K., Mori, K. and Mizuno, S. 114 J. Biochem. (Tokyo), 1-4 (1993); Tanaka, K., Kajiyama, N., Ishikura, K., Waga, S., Kikuchi, A., Ohtomo, K., Takagi, T. and Mizuno, S., 1432 Biochim. Biophys. Acta., 92-103 (1999); Y Kikuchi, K Mori, S Suzuki, K Yamaguchi and S Mizuno, "Structure of the *Bombyx mori* fibroin light-chain-encoding gene: upstream sequence elements common to the light and heavy chain," 110 Gene, 151-158 (1992) each of which are hereby incorporated by reference in their entirety herein). The sericins are a high molecular weight, soluble glycoprotein constituent of silk which gives the stickiness to the material. These glycoproteins are hydrophilic and can be easily removed from cocoons by boiling in water.

As used herein, the term "silk fibroin" refers to silk fibroin protein, whether produced by silkworm, spider, or other insect, or otherwise generated (Lucas et al., 13 Adv. Protein Chem., 107-242 (1958) hereby incorporated by reference in its entirety herein). In some embodiments, silk fibroin is obtained from a solution containing a dissolved silkworm silk or spider silk. For example, in some embodiments, silkworm silk fibroins are obtained, from the cocoon of *Bombyx mori*. In some embodiments, spider silk fibroins are obtained, for example, from *Nephila clavipes*. In the alternative, in some embodiments, silk fibroins suitable for use in the invention are obtained from a solution containing a genetically engineered silk harvested from bacteria, yeast, mammalian cells, transgenic animals or transgenic plants.

See, e.g., WO 97/08315 and U.S. Pat. No. 5,245,012, each of which is incorporated herein as reference in its entirety.

Thus, in some embodiments, a silk solution is used to fabricate compositions of the present disclosure contain fibroin proteins, essentially free of sericins. In some embodiments, silk solutions used to fabricate various compositions of the present disclosure contain the heavy chain of fibroin, but are essentially free of other proteins. In other embodiments, silk solutions used to fabricate various compositions of the present disclosure contain both the heavy and light chains of fibroin, but are essentially free of other proteins. In certain embodiments, silk solutions used to fabricate various compositions of the present disclosure include both a heavy and a light chain of silk fibroin; in some such embodiments, the heavy chain and the light chain of silk fibroin are linked via at least one disulfide bond. In some embodiments where the heavy and light chains of fibroin are present, they are linked via one, two, three or more disulfide bonds. Although different species of silk-producing organisms, and different types of silk, have different amino acid compositions, various fibroin proteins share certain structural features. A general trend in silk fibroin structure is a sequence of amino acids that is characterized by usually alternating glycine and alanine, or alanine alone. Such configuration allows fibroin molecules to self-assemble into a beta-sheet conformation. These "Alanine-rich" hydrophobic blocks are typically separated by segments of amino acids with bulky side-groups (e.g., hydrophilic spacers).

Silk materials explicitly exemplified herein were typically prepared from material spun by silkworm, *Bombyx mori*. In some embodiments, methods of providing, preparing, and/or manufacturing silk fibroin-based hydrogels of the present disclosure includes providing a silk solution. In some embodiments, a method of providing, preparing, and/or manufacturing silk fibroin-based hydrogels of the present disclosure includes boiling silk in $Na_2CO_3$ for about 10 minutes, about 20 minutes, about 30 minutes, or about 60 minutes. Typically, cocoons are boiled in an aqueous solution of 0.02 M $Na_2CO_3$, then rinsed thoroughly with water to extract the glue-like sericin proteins.

In some embodiments, polymers of silk fibroin fragments can be derived by degumming silk cocoons at or close to (e.g., within 5% around) an atmospheric boiling temperature for at least about: 1 minute of boiling, 2 minutes of boiling, 3 minutes of boiling, 4 minutes of boiling, 5 minutes of boiling, 6 minutes of boiling, 7 minutes of boiling, 8 minutes of boiling, 9 minutes of boiling, 10 minutes of boiling, 11 minutes of boiling, 12 minutes of boiling, 13 minutes of boiling, 14 minutes of boiling, 15 minutes of boiling, 16 minutes of boiling, 17 minutes of boiling, 18 minutes of boiling, 19 minutes of boiling, 20 minutes, 25 minutes of boiling, 30 minutes of boiling, 35 minutes of boiling, 40 minutes of boiling, 45 minutes of boiling, 50 minutes of boiling, 55 minutes of boiling, 60 minutes or longer, including, e.g., at least 70 minutes, at least 80 minutes, at least 90 minutes, at least 100 minutes, at least 110 minutes, at least about 120 minutes or longer. As used herein, the term "atmospheric boiling temperature" refers to a temperature at which a liquid boils under atmospheric pressure.

In some embodiments, hydrogels of the present disclosure produced from silk fibroin fragments can be formed by degumming silk cocoons in an aqueous solution at temperatures of: about 30° C., about 35° C., about 40° C., about 45° C., about 50° C., about 45° C., about 60° C., about 65° C., about 70° C., about 75° C., about 80° C., about 85° C., about 90° C., about 95° C., about 100° C., about 105° C., about 110° C., about 115° C., about at least 120° C.

In some embodiments, such elevated temperature can be achieved by carrying out at least portion of the heating process (e.g., boiling process) under pressure. For example, suitable pressure under which silk fibroin fragments described herein can be produced are typically between about 10-40 psi, e.g., about 11 psi, about 12 psi, about 13 psi, about 14 psi, about 15 psi, about 16 psi, about 17 psi, about 18 psi, about 19 psi, about 20 psi, about 21 psi, about 22 psi, about 23 psi, about 24 psi, about 25 psi, about 26 psi, about 27 psi, about 28 psi, about 29 psi, about 30 psi, about 31 psi, about 32 psi, about 33 psi, about 34 psi, about 35 psi, about 36 psi, about 37 psi, about 38 psi, about 39 psi, or about 40 psi.

Extracted silk is then dissolved in a solvent, for example, LiBr (such as 9.3 M) solution at room temperature. In some embodiments, silk fibers were solubilized in lithium bromide (LiBr) and then dialyzed against water to yield a polymer molecular weight of between about 3.5 kDa and about 350 kDa and a polymer concentration of between about 0.1 mg/mL and about 20 mg/mL. A resulting silk fibroin solution can then be further processed for a variety of applications as described elsewhere herein.

In some embodiments, provided silk fibroin-based hydrogels are modulated by controlling a silk concentration. In some embodiments, a weight percentage of silk fibroin can be present in the solution at any concentration suited to the need. In some embodiments, an aqueous silk fibroin solution can have silk fibroin at a concentration of about 0.1 mg/mL to about 20 mg/mL. In some embodiments, an aqueous silk fibroin solution can include silk fibroin at a concentration of about less than 1 mg/mL, about less than 1.5 mg/mL, about less than 2 mg/mL, about less than 2.5 mg/mL, about less than 3 mg/mL, about less than 3.5 mg/mL, about less than 4 mg/mL, about less than 4.5 mg/mL, about less than 5 mg/mL, about less than 5.5 mg/mL, about less than 6 mg/mL, about less than 6.5 mg/mL, about less than 7 mg/mL, about less than 7.5 mg/mL, about less than 8 mg/mL, about less than 8.5 mg/mL, about less than 9 mg/mL, about less than 9.5 mg/mL, about less than 10 mg/mL, about less than 11 mg/mL, about less than 12 mg/mL, about less than 13 mg/mL, about less than 14 mg/mL, about less than 15 mg/mL, about less than 16 mg/mL, about less than 17 mg/mL, about less than 18 mg/mL, about less than 19 mg/mL, or about less than 20 mg/mL.

In some embodiments, polymers refers to peptide chains or polypeptides having an amino acid sequence corresponding to fragments derived from silk fibroin protein or variants thereof. In the context of hydrogels of the present disclosure, silk fibroin fragments generally refer to silk fibroin peptide chains or polypeptides that are smaller than naturally occurring full length silk fibroin counterpart, such that one or more of the silk fibroin fragments within a population or composition. In some embodiments, for example, silk fibroin-based hydrogels include silk fibroin polypeptides having an average molecular weight of between about 3.5 kDa and about 350 kDa. In some embodiments, suitable ranges of silk fibroin fragments include, but are not limited to: silk fibroin polypeptides having an average molecular weight of between about 3.5 kDa and about 200 kDa; silk fibroin polypeptides having an average molecular weight of between about 3.5 kDa and about 150 kDa; silk fibroin polypeptides having an average molecular weight of between about 3.5 kDa and about 120 kDa. In some embodiments, silk fibroin polypeptides have an average molecular weight of: about 3.5 kDa, about 4 kDa, about 4.5 kDa, about 5 kDa, about 6 kDa, about 7 kDa, about 8 kDa, about 9 kDa, about 10 kDa, about 15 kDa, about 20 kDa, about 25 kDa, about 30 kDa, about 35 kDa, about 40 kDa, about 45 kDa, about 50 kDa, about 55 kDa, about 60 kDa, about 65 kDa, about 70 kDa, about 75 kDa, about 80 kDa, about 85 kDa, about 90 kDa, about 95 kDa, about 100 kDa, about 105 kDa, about 110 kDa, about 115 kDa, about 120 kDa, about 125 kDa, about 150 kDa, about 200 kDa, about 250 kDa, about 300 kDa, or about 350 kDa. In some preferred embodiments, silk fibroin polypeptides have an average molecular weight of about 100 kDa.

In some embodiments, silk fibroin-based hydrogels are or include silk fibroin and/or silk fibroin fragments. In some embodiments, silk fibroin and/or silk fibroin fragments of various molecular weights may be used. In some embodiments, silk fibroin and/or silk fibroin fragments of various molecular weights are silk fibroin polypeptides. In some embodiments, silk fibroin polypeptides are "reduced" in size, for instance, smaller than the original or wild type counterpart, may be referred to as "low molecular weight silk fibroin." In some embodiments, silk fibroin polypeptides have an average molecular weight of: less than 350 kDa, less than 300 kDa, less than 250 kDa, less than 200 kDa, less than 175 kDa, less than 150 kDa, less than 120 kDa, less than 100 kDa, less than 90 kDa, less than 80 kDa, less than 70 kDa, less than 60 kDa, less than 50 kDa, less than 40 kDa, less than 30 kDa, less than 25 kDa, less than 20 kDa, less than 15 kDa, less than 12 kDa, less than 10 kDa, less than 9 kDa, less than 8 kDa, less than 7 kDa, less than 6 kDa, less than 5 kDa, less than 4 kDa, less than 3.5 kDa, less than 3 kDa, less than 2.5 kDa, less than 2 kDa, less than 1.5 kDa, or less than about 1.0 kDa, etc.

In some embodiments, various technologies for obtaining or preparing low molecular weight silk fibroin fragments are known. To give but one example, it is known in the art that different molecular weight preparations of silk fibroin may be prepared or obtained by boiling silk solutions (e.g., as is typically done during degumming processes) for different amounts of time. For example, careful studies (see, for example, Wray et al., Effect of Processing on Silk-Based Biomaterials: Reproducibility and Biocompaticility, 99 J. Biomed. Mat. Res. Part B: Applied Biomaterials, 89-101 (epub 21 Jun. 2011), which is incorporated by reference in its entirety herein) of effects of different boiling times on silk fibroin solutions have established, among other things, that boiling for particular specific amounts of time results in silk fibroin compositions characterized by particular ranges of molecular weights. For example, under certain established conditions, boiling for 5 minutes results in preparations ("5 mb" preparations) characterized by relatively high molecular weight silk (e.g., within the range of about 300 kD-about 400 kD), boiling for 30 minutes results in preparations ("30 mb" preparations) characterized by a molecular weight distribution with a peak around 100 kD), and boiling for 60 minutes results in preparations ("60 mb" preparations) characterized by lower molecular weights (e.g., with a distribution that peaks around 60 kD).

Moreover, compositions boiled for these different times are known to have different material properties attributable to their different molecular weights, even when they show comparable β-sheet character. For example, as reported by Wray et al, report that initial degradation of samples boiled for longer times is faster than that of samples boiled for shorter times. Also, scaffold assembly from samples boiled for different periods of time resulted in distinct differences in macroscopic shape, pore size, and porosity. Specifically, both the 5 mb and 60 mb samples displayed a wide range of pore sizes, but the 60 mb sample displayed less pore interconnectivity. The 30 mb sample displayed homogenous pore samples that were highly interconnected. Viability of endothelial cells cultured in direct contact with silk films prepared from the variously-boiled samples also decreased as duration of boiling increased (and molecular weight decreased). Other studies (e.g., Tsubouchi et al *J Insect Biotechnol Sericol* 72:65, 2003 reported that human skin fibroblast cell viability remains strong (and improved relative to a control) for samples boiled for 5, 10, or 30 minutes; samples boiled for 60 min were reported to hinder cell viability.

In some embodiments, silk fibroin-based hydrogels are characterized in that they include submicron size or nano-sized crystallized spheres and/or particles. In some embodiments, such submicron size or nanosized crystallized spheres and/or particles have average diameters ranging between about 5 nm and 200 nm. In some embodiments, submicron size or nanosized crystallized spheres and/or particles have less than 150 nm average diameter, e.g., less than 145 nm, less than 140 nm, less than 135 nm, less than 130 nm, less than 125 nm, less than 120 nm, less than 115 nm, less than 110 nm, less than 100 nm, less than 90 nm, less than 80 nm, less than 70 nm, less than 60 nm, less than 50 nm, less than 40 nm, less than 30 nm, less than 20 nm, less than 15 nm, less than 10 nm, less than 5 nm, or smaller. In some preferred embodiments, submicron size or nanosized crystallized spheres and/or particles have average diameters of less than 100 nm.

In some embodiments, silk fibroin fragments solubilized prior to gelation. In some embodiments, a carrier can be a solvent or dispersing medium. In some embodiments, a solvent and/or dispersing medium, for example, is water, cell culture medium, buffers (e.g., phosphate buffered saline), a buffered solution (e.g. PBS), polyol (for example, glycerol, propylene glycol, liquid polyethylene glycol, and the like), Dulbecco's Modified Eagle Medium, fetal bovine serum, or suitable combinations and/or mixtures thereof.

In some embodiments, silk fibroin-based hydrogels are non-toxic. In some embodiments, silk fibroin-based hydrogels are biocompatible.

Optical Transparency

In some embodiments, silk fibroin-based hydrogels of the present disclosure are characterized by optical transparency in the visible spectrum.

In some embodiments, silk fibroin-based hydrogels exhibit increase optical clarity when compared with traditional hydrogels, such as collagen based hydrogels.

In some embodiments, silk fibroin-based hydrogels exhibit optical clarity in visual spectrum. In some embodiments, silk fibroin-based hydrogels transmit light in a wavelength range between about 400 nm to about 800 nm. In some embodiments, provided silk fibroin-based hydrogels are between about 50% and 100% transparent in the visible spectrum. In some embodiments, silk fibroin-based hydrogels are characterized by having a high degree of transparency, e.g., about 20% to 99% transmittance in the visible spectrum (wavelengths ranging between about 400-700 nm). In some embodiments, silk fibroin-based hydrogels are at least 35% transparent in the visible spectrum, at least 40% transparent in the visible spectrum, at least 45% transparent in the visible spectrum, at least 50% transparent in the visible spectrum, at least 55% transparent in the visible spectrum, at least 60% transparent in the visible spectrum, at least 65% transparent in the visible spectrum, at least 70% transparent in the visible spectrum, at least 75% transparent in the visible spectrum, at least 80% transparent in the visible spectrum, at least 85% transparent in the visible spectrum, at least 90% transparent in the visible spectrum, at least 91% transparent in the visible spectrum, at least 92% transparent in the visible spectrum, at least 93% transparent in the visible spectrum, at least 94% transparent in the visible spectrum, at least 95% transparent in the visible spectrum at least 96% transparent in the visible spectrum, at least 97% transparent in the visible spectrum, at least 98% transparent in the visible spectrum, at least 99% transparent in the visible spectrum, or greater transparency in the visible spectrum as determined by methods described herein. In some embodiments, silk fibroin-based hydrogels of the present disclosure are characterized by optical transmittance greater that 93% in the visible spectrum.

In some embodiments, silk fibroin-based hydrogels are and/or maintain optically transparency as above provided when they include additives, agents, or functional moieties.

Crystalline Silk Materials

As known in the art and as described herein, silk proteins can stack with one another in crystalline arrays.

In some embodiments, protein polymers for use in accordance with the present disclosure include amino acid phenolic side chains. In some embodiments, hydrogels are formed when polymer chains cross-link into networks through chemical or physical means. In some embodiments, amino acid phenolic side chains are tyrosine. In some embodiments, silk fibroin-based hydrogels include cross-linked amino acid phenolic side chains are dityrosine covalent bonds. In some embodiments, crosslinked phenolic amino acid side chain chains are covalently covalently crosslinked dityrosine bonds. The silk fibroin-based hydrogels include tyrosine crosslinks, which can enable beta sheet formation.

In some embodiments, provided hydrogels are characterized by crystalline structure comprising beta sheet structures and/or hydrogen bonding. In some embodiments, tyrosine silk fibroin hydrogels described herein can be resistant to extreme compression and show no plastic deformation at strains of at least 50%. In some embodiments, tyrosine covalently crosslinked gels can have an ability to swell, e.g., up to 400% of its original volume. In some embodiments, the tyrosine covalently crosslinked gels are a true elastomer, rather than a visco-elastic hydrogel. For example, tyrosine covalently crosslinked gels can exhibit negligible energy loss during deformation and nearly fully recover after deformation. For example, some conventional silk fibroin gels typically exhibit plastic deformation between 6-12% strain, while the tyrosine covalently crosslinked gels can be recoverable to compressive strains of at least 50%. In some embodiments, exemplified tyrosine silk fibroin hydrogels characterized by the above described properties can be formed from polymer solutions with a low weight percent concentration of polymer, for example, less than 10 wt %.

Various properties of such arrays are determined, for example, by the degree of beta-sheet structure in the material, the degree of crosslinking between such beta sheets, the presence (or absence) of certain dopants or other materials. In some embodiments, one or more of these features is intentionally controlled or engineered to achieve particular characteristics of a silk matrix. In some embodiments, silk fibroin-based hydrogels are characterized by crystalline structure, for example, comprising beta sheet structure and/or hydrogen bonding. In some embodiments, provided silk fibroin-based hydrogels are characterized by a percent beta sheet structure within the range of about 0% to about 45%. In some embodiments, silk fibroin-based hydrogels are characterized by crystalline structure, for example, comprising beta sheet structure of about 1%, about 2%, about 3%, about 4%, about 5%, about 6%, about 7%, about 8%, about 9%, about 10%, about 11%, about 12%, about 13%, about 1%, about 1%, about 1%, about 1%, about 1%, about 1%, about 1%, about 1%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, or about 45%.

In some embodiments, silk fibroin-based hydrogels are characterized as exhibiting crystallinity, nanosized crystalline particles, and optical transparency as described hereinabove at least part of which is facilitated by a sol-gel transition of a silk fibroin solution to a silk fibroin-based hydrogel via a nanogelation as provided herein.

Tunable Mechanical Properties

In some embodiments, mechanical properties of hydrogels of the present disclosure are tunable for use in different applications. In some embodiments, hydrogels may be tailored by tunable properties to specific needs, for example, cell engineering or tissue remodeling.

In some embodiments, silk fibroin-based hydrogels of the present disclosure may be "tuned", and, therefore possess "tunable properties," which provide flexibility both in structure and application. In some embodiments, mechanical properties, in particular compressive strength, compressive modulus, stress-strain are tunable. In some embodiments, silk fibroin-based hydrogels with tunable properties are characterized in that they exhibit improved structural stability corresponding to increased compressive strength and/or increased compressive modulus. In some embodiments, silk fibroin-based hydrogels of the present disclosure are characterized by highly tunable mechanical properties. In some embodiments, silk fibroin-based hydrogels of the present disclosure are characterized in that they possess mechanical properties that are tunable to a particular desired range and/or set. In some embodiments, mechanical properties, in particular compressive strength and compressive modulus are tunable.

Porosity

In some embodiments, hydrogel form a porous matrix or scaffold. In some embodiments, silk fibroin-based hydrogels of the present disclosure may have pores therein, i.e., a measurable degree of porosity. For example, in some embodiments, provided silk fibroin-based hydrogels have a porosity of between about 0% and 50%, e.g., about 5%, about 10%, about 15%, about 20%, about 25%, about 30%, about 35%, about 40%, about 45%, about 50%, etc. Suitable porogens, for example, may be used to achieve desired porosity.

Recovery from Strain or Compression

In some embodiments, provided hydrogels of the present disclosure are characterized by high stiffness and superior resilience and elasticity. In some embodiments, provided hydrogels of the present disclosure are characterized in that they fully recover from large strains or long term cyclic compressions. In some embodiments, provided hydrogels of the present disclosure are characterized in that they withstand long term stress with negligible changes in modulus and without showing an indication of appreciable changes in mechanical properties, such as a plastic deformation. In some embodiments, provided hydrogels of the present disclosure are characterized in that they are capable of withstanding repeated strains. In some embodiments, provided hydrogels of the present disclosure that have been shown to exhibit the above identified characteristics and/or properties are formed from solutions of low weight percent concentration of polymer and of low molecular weight polymers.

In some embodiments, a compressive strength of silk fibroin-based hydrogels is tunable. In some embodiments, a compressive strength of silk fibroin-based hydrogels is tunable in a range of between about 0.5 kPa and about 12 kPa without showing an indication of a plastic deformation. In some embodiments, silk fibroin-based hydrogels show a compressive strength of about 0.5 kPa, about 1 kPa, about 1.5 kPa, about 2 kPa, about 2.5 kPa, about 3 kPa, about 3.5 kPa, about 4 kPa, about 4.5 kPa, about 5 kPa, about 5.5 kPa, about 6 kPa, about 7 kPa, about 8 kPa, about 9 kPa, about 10 kPa, about 11 kPa, or about 12 kPa without showing an indication of a plastic deformation.

In some embodiments, a compressive modulus of silk fibroin-based hydrogels is tunable. In some embodiments, a compressive modulus of silk fibroin-based hydrogels is tunable in a range of between about 0.5 kPa and about 20 kPa without showing an indication of a plastic deformation. In some embodiments, silk fibroin-based hydrogels show a compressive modulus of about 0.5 kPa, about 1 kPa, about 2 kPa, about 3 kPa, about 4 kPa, about 5 kPa, about 6 kPa, about 7 kPa, about 8 kPa, about 9 kPa, about 10 kPa, about 11 kPa, about 12 kPa, about 13 kPa, about 14 kPa, about 15 kPa, about 16 kPa, about 17 kPa, about 18 kPa, about 19 kPa or about 20 kPa without showing an indication of a plastic deformation.

In some embodiments, a compressive modulus of silk fibroin-based hydrogels is tunable in a range of between about 0.5 kPa and about 20 kPa without showing an indication of a plastic deformation when measure at crosshead rates of: 0.100 mm/min, 0.200 mm/min, and/or 2.00 mm/min.

Crosslink density can be measured using a swelling ratio. (See e.g. Ding, Z. Y., et al., Model filled polymers; VI. Determination of the crosslink density of polymeric beads by swelling, 29 Journal of Polymer Science Part B: Polymer Physics 8, 1035-1038 (1991); see also ASTM D2765-95 Standard Test Methods for Determination of Gel Content and Swell Ratio of Crosslinked Ethylene Plastics).

Hydrogel stiffness has been shown to correlate with crosslink density. (See S. Lin, Influence of Crosslink Density and Stiffness on Mechanical Properties of Type I Collagen Gel, 8 Materials, 551-560 (2015); (showing that a range of collagen hydrogel stiffness values lends to a range of crosslink densities)).

In some embodiments, crosslink density correlates with hydrogel stiffness. In some embodiments, an increase in hydrogel stiffness correlates with an increase in crosslink density. In some embodiments, an increase in hydrogel stiffness of about 25× to about 125× correlates with an increase in crosslink density about 2× to about 10×.

In some embodiments, characteristics of silk fibroin-based hydrogels are tuned according to fabrication conditions (e.g., molecular weight of silk fibroin, a concentration of silk fibroin present in solution from which the silk fibroin-based hydrogels are prepared, etc.).

Additives, Agents, and/or Functional Moieties

In some embodiments, silk fibroin-based hydrogels include additives, agents, or functional moieties.

In some embodiments, hydrogels of the present disclosure provide ease of incorporation of functional components. In some embodiments, suitable gel functionalization is tunable to specific cell and/or tissue needs. In some embodiments, hydrogels of the present disclosure are suitable for functionalization or inclusion of components to support needs of cell engineering or tissue remodeling. In some embodiments, channels molded into scaffolds of materials of the present disclosure support cell infiltration, for example for soft tissue repair and/or replacement by enhancing diffusion of oxygen and nutrients and promoting vascularization in critically sized defects.

In some embodiments, silk fibroin-based hydrogels degrade to release an agent useful for treatment of a disease, disorder, or condition.

In some embodiments, provided hydrogels can include one or more (e.g., one, two, three, four, five or more) agents and/or functional moieties (together, "additives"). Without wishing to be bound by a theory additive can provide or enhance one or more desirable properties, e.g., strength, flexibility, ease of processing and handling, biocompatibility, bioresorability, surface morphology, release rates and/or kinetics of one or more active agents present in the composition, and the like. In some embodiments, one or more such additives can be covalently or non-covalently linked with the hydrogel (e.g., with a polymer such as silk fibroin that makes up the hydrogel) and can be integrated homogenously or heterogeneously within the silk composition.

In some embodiments, an additive is or includes a moiety covalently associated (e.g., via chemical modification or genetic engineering) with a polymer. In some embodiments, an addivity is non-covalently associated with a hydrogel or hydrogel component.

In some embodiments, provided hydrogels include additives at a total amount from about 0.01 wt % to about 99 wt %, from about 0.01 wt % to about 70 wt %, from about 5 wt % to about 60 wt %, from about 10 wt % to about 50 wt %, from about 15 wt % to about 45 wt %, or from about 20 wt % to about 40 wt %, of the total silk composition. In some embodiments, ratio of silk fibroin to additive in the composition can range from about 1000:1 (w/w) to about 1:1000 (w/w), from about 500:1 (w/w) to about 1:500 (w/w), from about 250:1 (w/w) to about 1:250 (w/w), from about 200:1 (w/w) to about 1:200 (w/w), from about 25:1 (w/w) to about 1:25 (w/w), from about 20:1 (w/w) to about 1:20 (w/w), from about 10:1 (w/w) to about 1:10 (w/w), or from about 5:1 (w/w) to about 1:5 (w/w).

In some embodiments, provided hydrogels include one or more additives at a molar ratio relative to polymer (i.e., a polymer:additive ratio) of, e.g., at least 1000:1, at least 900:1, at least 800:1, at least 700:1, at least 600:1, at least 500:1, at least 400:1, at least 300:1, at least 200:1, at least 100:1, at least 90:1, at least 80:1, at least 70:1, at least 60:1, at least 50:1, at least 40:1, at least 30:1, at least 20:1, at least 10:1, at least 7:1, at least 5:1, at least 3:1, at least 1:1, at least 1:3, at least 1:5, at least 1:7, at least 1:10, at least 1:20, at least 1:30, at least 1:40, at least 1:50, at least 1:60, at least 1:70, at least 1:80, at least 1:90, at least 1:100, at least 1:200, at least 1:300, at least 1:400, at least 1:500, at least 600, at least 1:700, at least 1:800, at least 1:900, or at least 1:100.

In some embodiments, moiety polymer:additive ratio is, e.g., at most 1000:1, at most 900:1, at most 800:1, at most 700:1, at most 600:1, at most 500:1, at most 400:1, at most 300:1, at most 200:1, 100:1, at most 90:1, at most 80:1, at most 70:1, at most 60:1, at most 50:1, at most 40:1, at most 30:1, at most 20:1, at most 10:1, at most 7:1, at most 5:1, at most 3:1, at most 1:1, at most 1:3, at most 1:5, at most 1:7, at most 1:10, at most 1:20, at most 1:30, at most 1:40, at most 1:50, at most 1:60, at most 1:70, at most 1:80, at most 1:90, at most 1:100, at most 1:200, at most 1:300, at most 1:400, at most 1:500, at most 1:600, at most 1:700, at most 1:800, at most 1:900, or at most 1:1000.

In some embodiments, moiety polymer:additive ratio is, e.g., from about 1000:1 to about 1:1000, from about 900:1 to about 1:900, from about 800:1 to about 1:800, from about 700:1 to about 1:700, from about 600:1 to about 1:600, from about 500:1 to about 1:500, from about 400:1 to about 1:400, from about 300:1 to about 1:300, from about 200:1 to about 1:200, from about 100:1 to about 1:100, from about 90:1 to about 1:90, from about 80:1 to about 1:80, from about 70:1 to about 1:70, from about 60:1 to about 1:60, from about 50:1 to about 1:50, from about 40:1 to about 1:40, from about 30:1 to about 1:30, from about 20:1 to about 1:20, from about 10:1 to about 1:10, from about 7:1 to about 1:7, from about 5:1 to about 1:5, from about 3:1 to about 1:3, or about 1:1.

In some embodiments, silk fibroin-based hydrogels with tunable properties are characterized in that they exhibit improved structural stability corresponding to increased compressive strength and/or increased compressive modulus. In some embodiments, at least part of such elasticity or compressive ability may be facilitated by crosslinking agent. In some embodiments, for example, one or more crosslinking agents may be used to achieve crosslinking of silk fibroin polypeptides, intra-molecularly, inter-molecularly, or both. Any suitable crosslinking agents may be used, including but are not limited to: an amine-to-amine crosslinker, amine-to-sulfhydryl crosslinker, carboxyl-to-amine crosslinker, photoreactive crosslinker, sulfhydryl-to-carbohydrate crosslinker, sulfhydryl-to-hydroxyl crosslinker, sulfhydryl-to-sulfhydryl crosslinker, or any combination thereof.

In some embodiments, provided hydrogels include additives, for example, therapeutic, preventative, and/or diagnostic agents.

In some embodiments, an additive is or includes one or more therapeutic agents. In general, a therapeutic agent is or includes a small molecule and/or organic compound with pharmaceutical activity (e.g., activity that has been demonstrated with statistical significance in one or more relevant pre-clinical models or clinical settings). In some embodiments, a therapeutic agent is a clinically-used drug. In some embodiments, a therapeutic agent is or includes an cells, proteins, peptides, nucleic acid analogues, nucleotides, oligonucleotides, nucleic acids (DNA, RNA, siRNA), peptide nucleic acids, aptamers, antibodies or fragments or portions thereof, anesthetic, anticoagulant, anti-cancer agent, inhibitor of an enzyme, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, anti-glaucoma agent, neuroprotectant, angiogenesis inhibitor, hormones, hormone antagonists, growth factors or recombinant growth factors and fragments and variants thereof, cytokines, enzymes, antibiotics or antimicrobial compounds, antifungals, antivirals, toxins, prodrugs, chemotherapeutic agents, small molecules, drugs (e.g., drugs, dyes, amino acids, vitamins, antioxidants), pharmacologic agents, and combinations thereof.

In some embodiments, provided hydrogels include additives, for example, cells. Cells suitable for use herein include, but are not limited to, progenitor cells or stem cells, smooth muscle cells, skeletal muscle cells, cardiac muscle cells, epithelial cells, endothelial cells, urothelial cells, fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, and precursor cells.

In some embodiments, provided hydrogels include additives, for example, organisms, such as, a bacterium, fungus, plant or animal, or a virus. In some embodiments, an active agent may include or be selected from neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents may also include therapeutic compounds, such as pharmacological materials, vitamins, sedatives, hypnotics, prostaglandins and radiopharmaceuticals.

In some embodiments, silk fibroin-based hydrogels are characterized in that when seeded cells would culture on a hydrogel surface. In some embodiments, cells would remain viable for a period up to 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 35 days, 40 days, 45 days, 50 days, 55 days, 60 days, or 65 days.

In some embodiments, provided hydrogels include additives, for example, antibiotics. Antibiotics suitable for incorporation in hydrogels include, but are not limited to, aminoglycosides (e.g., neomycin), ansamycins, carbacephem, carbapenems, cephalosporins (e.g., cefazolin, cefaclor, cefditoren, cefditoren, ceftobiprole), glycopeptides (e.g., vancomycin), macrolides (e.g., erythromycin, azithromycin), monobactams, penicillins (e.g., amoxicillin, ampicillin, cloxacillin, dicloxacillin, flucloxacillin), polypeptides (e.g., bacitracin, polymyxin B), quinolones (e.g., ciprofloxacin, enoxacin, gatifloxacin, ofloxacin, etc.), sulfonamides (e.g., sulfasalazine, trimethoprim, trimethoprim-sulfamethoxazole (co-trimoxazole)), tetracyclines (e.g., doxycyline, minocycline, tetracycline, etc.), chloramphenicol, lincomycin, clindamycin, ethambutol, mupirocin, metronidazole, pyrazinamide, thiamphenicol, rifampicin, thiamphenicl, dapsone, clofazimine, quinupristin, metronidazole, linezolid, isoniazid, fosfomycin, fusidic acid, β-lactam antibiotics, rifamycins, novobiocin, fusidate sodium, capreomycin, colistimethate, gramicidin, doxycycline, erythromycin, nalidixic acid, and vancomycin. For example, β-lactam antibiotics can be aziocillin, aztreonam, carbenicillin, cefoperazone, ceftriaxone, cephaloridine, cephalothin, moxalactam, piperacillin, ticarcillin and combination thereof.

In some embodiments, provided hydrogels include additives, for example, anti-inflammatories. Anti-inflammatory agents may include corticosteroids (e.g., glucocorticoids), cycloplegics, non-steroidal anti-inflammatory drugs (NSAIDs), immune selective anti-inflammatory derivatives (ImSAIDs), and any combination thereof. Exemplary NSAIDs include, but not limited to, celecoxib (Celebrex®); rofecoxib (Vioxx®), etoricoxib (Arcoxia®), meloxicam (Mobic®), valdecoxib, diclofenac (Voltaren®, Cataflam®), etodolac (Lodine®), sulindac (Clinori®), aspirin, alclofenac, fenclofenac, diflunisal (Dolobid®), benorylate, fosfosal, salicylic acid including acetylsalicylic acid, sodium acetylsalicylic acid, calcium acetylsalicylic acid, and sodium salicylate; ibuprofen (Motrin), ketoprofen, carprofen, fenbufen, flurbiprofen, oxaprozin, suprofen, triaprofenic acid, fenoprofen, indoprofen, piroprofen, flufenamic, mefenamic, meclofenamic, niflumic, salsalate, rolmerin, fentiazac, tilomisole, oxyphenbutazone, phenylbutazone, apazone, feprazone, sudoxicam, isoxicam, tenoxicam, piroxicam (Feldene®), indomethacin (Indocin®), nabumetone (Relafen®), naproxen (Naprosyn®), tolmetin, lumiracoxib, parecoxib, licofelone (ML3000), including pharmaceutically acceptable salts, isomers, enantiomers, derivatives, prodrugs, crystal polymorphs, amorphous modifications, co-crystals and combinations thereof.

In some embodiments, provided hydrogels include additives, for example, antibodies. Suitable antibodies for incorporation in hydrogels include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab.

In some embodiments, provided hydrogels include additives, for example, polypeptides (e.g., proteins), including but are not limited to: one or more antigens, cytokines, hormones, chemokines, enzymes, and any combination thereof as an agent and/or functional group. Exemplary enzymes suitable for use herein include, but are not limited to, peroxidase, lipase, amylose, organophosphate dehydrogenase, ligases, restriction endonucleases, ribonucleases, DNA polymerases, glucose oxidase, laccase, and the like.

In some embodiments, provided hydrogels include additives, for example, particularly useful for wound healing. In some embodiments, agents useful for wound healing include stimulators, enhancers or positive mediators of the wound healing cascade which 1) promote or accelerate the natural wound healing process or 2) reduce effects associated with improper or delayed wound healing, which effects include, for example, adverse inflammation, epithelialization, angiogenesis and matrix deposition, and scarring and fibrosis.

In some embodiments, provided hydrogels include additives, for example, an optically or electrically active agent, including but not limited to, chromphores; light emitting organic compounds such as luciferin, carotenes; light emitting inorganic compounds, such as chemical dyes; light harvesting compounds such as chlorophyll, bacteriorhodopsin, protorhodopsin, and porphyrins; light capturing complexes such as phycobiliproteins; and related electronically active compounds; and combinations thereof.

Nucleic Acids

In some embodiments, provided hydrogels include additives, for example, nucleic acid agents. In some embodiments, a hydrogel may release nucleic acid agents. In some embodiments, a nucleic acid agent is or includes a therapeutic agent. In some embodiments, a nucleic acid agent is or includes a diagnostic agent. In some embodiments, a nucleic acid agent is or includes a prophylactic agent.

It would be appreciate by those of ordinary skill in the art that a nucleic acid agent can have a length within a broad range. In some embodiments, a nucleic acid agent has a nucleotide sequence of at least about 40, for example at least about 60, at least about 80, at least about 100, at least about 200, at least about 500, at least about 1000, or at least about 3000 nucleotides in length. In some embodiments, a nucleic acid agent has a length from about 6 to about 40 nucleotides. For example, a nucleic acid agent may be from about 12 to about 35 nucleotides in length, from about 12 to about 20 nucleotides in length or from about 18 to about 32 nucleotides in length.

In some embodiments, nucleic acid agents may be or include deoxyribonucleic acids (DNA), ribonucleic acids (RNA), peptide nucleic acids (PNA), morpholino nucleic acids, locked nucleic acids (LNA), glycol nucleic acids (GNA), threose nucleic acids (TNA), and/or combinations thereof.

In some embodiments, a nucleic acid has a nucleotide sequence that is or includes at least one protein-coding element. In some embodiments, a nucleic acid has a nucleotide sequence that is or includes at least one element that is a complement to a protein-coding sequence. In some embodiments, a nucleic acid has a nucleotide sequence that includes one or more gene expression regulatory elements (e.g., promoter elements, enhancer elements, splice donor sites, splice acceptor sites, transcription termination sequences, translation initiation sequences, translation termination sequences, etc.). In some embodiments, a nucleic acid has a nucleotide sequence that includes an origin of replication. In some embodiments, a nucleic acid has a nucleotide sequence that includes one or more integration sequences. In some embodiments, a nucleic acid has a nucleotide sequence that includes one or more elements that participate in intra- or inter-molecular recombination (e.g., homologous recombination). In some embodiments, a nucleic acid has enzymatic activity. In some embodiments, a nucleic acid hybridizes with a target in a cell, tissue, or organism. In some embodiments, a nucleic acid acts on (e.g., binds with, cleaves, etc.) a target inside a cell. In some embodiments, a nucleic acid is expressed in a cell after release from a provided composition. In some embodiments, a nucleic acid integrates into a genome in a cell after release from a provided composition.

In some embodiments, nucleic acid agents have single-stranded nucleotide sequences. In some embodiments, nucleic acid agents have nucleotide sequences that fold into higher order structures (e.g., double and/or triple-stranded structures). In some embodiments, a nucleic acid agent is or includes an oligonucleotide. In some embodiments, a nucleic acid agent is or includes an antisense oligonucleotide. Nucleic acid agents may include a chemical modification at the individual nucleotide level or at the oligonucleotide backbone level, or it may have no modifications.

In some embodiments of the present disclosure, a nucleic acid agent is an siRNA agent. Short interfering RNA (siRNA) includes an RNA duplex that is approximately 19 basepairs long and optionally further includes one or two single-stranded overhangs. An siRNA may be formed from two RNA molecules that hybridize together, or may alternatively be generated from a single RNA molecule that includes a self-hybridizing portion. It is generally preferred that free 5' ends of siRNA molecules have phosphate groups, and free 3' ends have hydroxyl groups. The duplex portion of an siRNA may, but typically does not, contain one or more bulges consisting of one or more unpaired nucleotides. One strand of an siRNA includes a portion that hybridizes with a target transcript. In certain preferred embodiments of the invention, one strand of the siRNA is precisely complementary with a region of the target transcript, meaning that the siRNA hybridizes to the target transcript without a single mismatch. In other embodiments of the invention one or more mismatches between the siRNA and the targeted portion of the target transcript may exist. In most embodiments of the invention in which perfect complementarity is not achieved, it is generally preferred that any mismatches be located at or near the siRNA termini.

Short hairpin RNA refers to an RNA molecule comprising at least two complementary portions hybridized or capable of hybridizing to form a double-stranded (duplex) structure sufficiently long to mediate RNAi (typically at least 19 base pairs in length), and at least one single-stranded portion, typically between approximately 1 and 10 nucleotides in length that forms a loop. The duplex portion may, but typically does not, contain one or more bulges consisting of one or more unpaired nucleotides. As described further below, shRNAs are thought to be processed into siRNAs by the conserved cellular RNAi machinery. Thus shRNAs are precursors of siRNAs and are, in general, similarly capable of inhibiting expression of a target transcript.

In describing siRNAs it will frequently be convenient to refer to sense and antisense strands of the siRNA. In general, the sequence of the duplex portion of the sense strand of the siRNA is substantially identical to the targeted portion of the target transcript, while the antisense strand of the siRNA is substantially complementary to the target transcript in this region as discussed further below. Although shRNAs contain a single RNA molecule that self-hybridizes, it will be appreciated that the resulting duplex structure may be considered to include sense and antisense strands or portions. It will therefore be convenient herein to refer to sense and antisense strands, or sense and antisense portions, of an shRNA, where the antisense strand or portion is that segment of the molecule that forms or is capable of forming a duplex and is substantially complementary to the targeted portion of the target transcript, and the sense strand or portion is that segment of the molecule that forms or is capable of forming a duplex and is substantially identical in sequence to the targeted portion of the target transcript.

For purposes of description, the discussion below may refer to siRNA rather than to siRNA or shRNA. However, as will be evident to one of ordinary skill in the art, teachings relevant to the sense and antisense strand of an siRNA are generally applicable to the sense and antisense portions of the stem portion of a corresponding shRNA. Thus in general the considerations below apply also to shRNAs.

An siRNA agent is considered to be targeted to a target transcript for the purposes described herein if 1) the stability of the target transcript is reduced in the presence of the siRNA or shRNA as compared with its absence; and/or 2) the siRNA or shRNA shows at least about 90%, more preferably at least about 91%, 92%, 93%, 94%, 95%, 96%, 97%, 98%, 99%, or 100% precise sequence complementarity with the target transcript for a stretch of at least about 15, more preferably at least about 17, yet more preferably at least about 18 or 19 to about 21-23 nucleotides; and/or 3) one strand of the siRNA or one of the self-complementary portions of the shRNA hybridizes to the target transcript under stringent conditions for hybridization of small (<50 nucleotide) RNA molecules in vitro and/or under conditions typically found within the cytoplasm or nucleus of mammalian cells. Since the effect of targeting a transcript is to reduce or inhibit expression of the gene that directs synthesis of the transcript, an siRNA, shRNA, targeted to a transcript is also considered to target the gene that directs synthesis of the transcript even though the gene itself (i.e., genomic DNA) is not thought to interact with the siRNA, shRNA, or components of the cellular silencing machinery. Thus in some embodiments, an siRNA, shRNA, that targets a transcript is understood to target the gene that provides a template for synthesis of the transcript.

In some embodiments, an siRNA agent can inhibit expression of a polypeptide (e.g., a protein). Exemplary polypeptides include, but are not limited to, matrix metallopeptidase 9 (MMP-9), neutral endopeptidase (NEP) and protein tyrosine phosphatase 1B (PTP1B).

Growth Factor

In some embodiments, provided hydrogels include additives, for example, growth factor. In some embodiments, a hydrogel may release growth factor. In some embodiments, a hydrogel may release multiple growth factors. In some embodiments growth factor known in the art include, for example, adrenomedullin, angiopoietin, autocrine motility factor, basophils, brain-derived neurotrophic factor, bone morphogenetic protein, colony-stimulating factors, connective tissue growth factor, endothelial cells, epidermal growth factor, erythropoietin, fibroblast growth factor, fibroblasts, glial cell line-derived neurotrophic factor, granulocyte colony stimulating factor, granulocyte macrophage colony stimulating factor, growth differentiation factor-9, hepatocyte growth factor, hepatoma-derived growth factor, insulin-like growth factor, interleukins, keratinocyte growth factor, keratinocytes, lymphocytes, macrophages, mast cells, myostatin, nerve growth factor, neurotrophins, platelet-derived growth factor, placenta growth factor, osteoblasts, platelets, proinflammatory, stromal cells, T-lymphocytes, thrombopoietin, transforming growth factor alpha, transforming growth factor beta, tumor necrosis factor-alpha, vascular endothelial growth factor and combinations thereof.

In some embodiments, provided hydrogels include additives, for example, that are particularly useful for healing. Exemplary agents useful as growth factor for defect repair and/or healing can include, but are not limited to, growth factors for defect treatment modalities now known in the art or later-developed; exemplary factors, agents or modalities including natural or synthetic growth factors, cytokines, or modulators thereof to promote bone and/or tissue defect healing. Suitable examples may include, but not limited to 1) topical or dressing and related therapies and debriding agents (such as, for example, Santyl® collagenase) and Iodosorb® (cadexomer iodine); 2) antimicrobial agents, including systemic or topical creams or gels, including, for example, silver-containing agents such as SAGs (silver antimicrobial gels), (CollaGUARD™, Innocoll, Inc) (purified type-I collagen protein based dressing), CollaGUARD Ag (a collagen-based bioactive dressing impregnated with silver for infected wounds or wounds at risk of infection), DermaSIL™ (a collagen-synthetic foam composite dressing for deep and heavily exuding wounds); 3) cell therapy or bioengineered skin, skin substitutes, and skin equivalents, including, for example, Dermograft (3-dimensional matrix cultivation of human fibroblasts that secrete cytokines and growth factors), Apligraf® (human keratinocytes and fibroblasts), Graftskin® (bilayer of epidermal cells and fibroblasts that is histologically similar to normal skin and produces growth factors similar to those produced by normal skin), TransCyte (a Human Fibroblast Derived Temporary Skin Substitute) and Oasis® (an active biomaterial that includes both growth factors and extracellular matrix components such as collagen, proteoglycans, and glycosaminoglycans); 4) cytokines, growth factors or hormones (both natural and synthetic) introduced to the wound to promote wound healing, including, for example, NGF, NT3, BDGF, integrins, plasmin, semaphoring, blood-derived growth factor, keratinocyte growth factor, tissue growth factor, TGF-alpha, TGF-beta, PDGF (one or more of the three subtypes may be used: AA, AB, and B), PDGF-BB, TGF-beta 3, factors that modulate the relative levels of TGFβ3, TGFβ1, and TGFβ2 (e.g., Mannose-6-phosphate), sex steroids, including for example, estrogen, estradiol, or an oestrogen receptor agonist selected from the group consisting of ethinyloestradiol, dienoestrol, mestranol, oestradiol, oestriol, a conjugated oestrogen, piperazine oestrone sulphate, stilboestrol, fosfesterol tetrasodium, polyestradiol phosphate, tibolone, a phytoestrogen, 17-beta-estradiol; thymic hormones such as Thymosin-beta-4, EGF, HB-EGF, fibroblast growth factors (e.g., FGF1, FGF2, FGF7), keratinocyte growth factor, TNF, interleukins family of inflammatory response modulators such as, for example, IL-10, IL-1, IL-2, IL-6, IL-8, and IL-10 and modulators thereof; INFs (INF-alpha, -beta, and -delta); stimulators of activin or inhibin, and inhibitors of interferon gamma prostaglandin E2 (PGE2) and of mediators of the adenosine 3',5'-cyclic monophosphate (cAMP) pathway; adenosine A1 agonist, adenosine A2 agonist or 5) other agents useful for wound healing, including, for example, both natural or synthetic homologues, agonist and antagonist of VEGF, VEGFA, IGF; IGF-1, proinflammatory cytokines, GM-CSF, and leptins and 6) IGF-1 and KGF cDNA, autologous platelet gel, hypochlorous acid (Sterilox®) lipoic acid, nitric oxide synthase3, matrix metalloproteinase 9 (MMP-9), CCT-ETA, alphavbeta6 integrin, growth factor-primed fibroblasts and Decorin, silver containing wound dressings, Xenaderm™, papain wound debriding agents, lactoferrin, substance P, collagen, and silver-ORC, placental alkaline phosphatase or placental growth factor, modulators of hedgehog signaling, modulators of cholesterol synthesis pathway, and APC (Activated Protein C), keratinocyte growth factor, TNF, Thromboxane A2, NGF, BMP bone morphogenetic protein, CTGF (connective tissue growth factor), wound healing chemokines, decorin, modulators of lactate induced neovascularization, cod liver oil, placental alkaline phosphatase or placental growth factor, and thymosin beta 4. In certain embodiments, one, two three, four, five or six agents useful for wound healing may be used in combination. More details can be found in U.S. Pat. No. 8,247,384, the contents of which are incorporated herein by reference.

It is to be understood that agents useful for growth factor for healing (including for example, growth factors and cytokines) above encompass all naturally occurring polymorphs (for example, polymorphs of the growth factors or cytokines). Also, functional fragments, chimeric proteins comprising one of said agents useful for wound healing or a functional fragment thereof, homologues obtained by analogous substitution of one or more amino acids of the wound healing agent, and species homologues are encompassed. It is contemplated that one or more agents useful for wound healing may be a product of recombinant DNA technology, and one or more agents useful for wound healing may be a product of transgenic technology. For example, platelet derived growth factor may be provided in the form of a recombinant PDGF or a gene therapy vector comprising a coding sequence for PDGF.

In some embodiments, provided hydrogels include additives, for example, that are particularly useful as diagnostic agents. In some embodiments, diagnostic agents include gases; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

In some embodiments, provided hydrogels include additives, for example, radionuclides that are particularly useful as therapeutic and/or diagnostic agents. Among the radionuclides used, gamma-emitters, positron-emitters, and X-ray emitters are suitable for diagnostic and/or therapy, while beta emitters and alpha-emitters may also be used for therapy. Suitable radionuclides for forming thermally-responsive conjugates in accordance with the invention include, but are not limited to, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101}$mRh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99m}$Tc, $^{14}$C, $^{13}$N, $^{15}$O, $^{32}$P, $^{33}$P, and $^{18}$F. In some embodiments, a diagnostic agent may be a fluorescent, luminescent, or magnetic moiety.

Fluorescent and luminescent moieties include a variety of different organic or inorganic small molecules commonly referred to as "dyes," "labels," or "indicators." Examples include fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Application Publication No.: 2004/0067503; Valeur, B., "Molecular Fluorescence: Principles and Applications," John Wiley and Sons, 2002; *Handbook of Fluorescent Probes and Research Products*, Molecular Probes, 9$^{th}$ edition, 2002; and *The Handbook—A Guide to Fluorescent Probes and Labeling Technologies*, Invitrogen, 10$^{th}$ edition, available at the Invitrogen web site; both of which are incorporated herein by reference).

Degradation Properties of Silk-Based Materials

In some embodiments, silk fibroin-based hydrogels are biodegradable.

Additionally, as will be appreciated by those of skill in the art, much work has established that researchers have the ability to control the degradation process of silk. According to the present disclosure, such control can be particularly valuable in the fabrication of electronic components, and particularly of electronic components that are themselves and/or are compatible with biomaterials. Degradability (e.g., bio-degradability) is often essential for biomaterials used in tissue engineering and implantation. The present disclosure encompasses the recognition that such degradability is also relevant to and useful in the fabrication of silk electronic components.

According to the present disclosure, one particularly desirable feature of silk-based materials is the fact that they can be programmably degradable. That is, as is known in the art, depending on how a particular silk-based material is prepared, it can be controlled to degrade at certain rates. Degradability and controlled release of a substance from silk-based materials have been published (see, for example, WO 2004/080346, WO 2005/012606, WO 2005/123114, WO 2007/016524, WO 2008/150861, WO 2008/118133, each of which is incorporated by reference herein).

Control of silk material production methods as well as various forms of silk-based materials can generate silk compositions with known degradation properties. For example, using various silk fibroin materials (e.g., microspheres of approximately 2 μm in diameter, silk film, silk hydrogels) entrapped agents such as therapeutics can be loaded in active form, which is then released in a controlled fashion, e.g., over the course of minutes, hours, days, weeks to months. It has been shown that layered silk fibroin coatings can be used to coat substrates of any material, shape and size, which then can be used to entrap molecules for controlled release, e.g., 2-90 days.

Flavins, Flavin Compounds, and Flavin Solutions

In some embodiments, a silk fibroin solution is combined with a flavin compound or mixed with a solution including a flavin compound. In some embodiments, a flavin compound includes a flavin group.

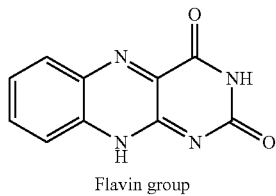 [SMILES: O=c1nc2[nH]c3ccccc3nc-2c(=O)[nH]1]

Flavin group

In some embodiments, a flavin compound is or includes riboflavin.

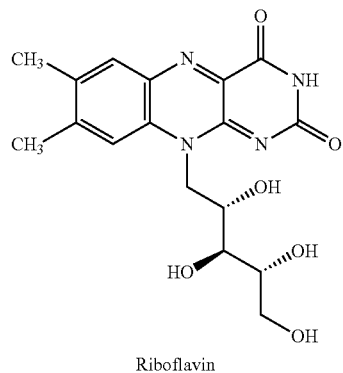 [SMILES: Cc1cc2nc3c(=O)[nH]c(=O)nc-3n(C[C@H](O)[C@H](O)[C@H](O)CO)c2cc1C]

Riboflavin

In some embodiments, a flavin compound is or includes flavin mononucleotide. In some embodiments, a flavin compound is or includes flavin adenine dinucleotide. In some embodiments, a flavin compound is or includes a flavin ring, flavin group, or flavin moiety. In some embodiments, a flavin compound is capable of an oxidation-reduction reaction. In some embodiments, a flavin compound is or includes 5'-monophosphate (FMN).

In some embodiments, a solvent is or include water. In some embodiments, a flavin compound is soluble in other non-aqueous solvents, such as culture medium, buffers (e.g., phosphate buffered saline), a buffered solution (e.g. PBS), polyol (for example, glycerol, propylene glycol, liquid polyethylene glycol, and the like) or suitable combinations or mixtures thereof.

In some embodiments, flavin solutions include a concentration between 0.05 mM and 1 M. In some embodiments, a concentration of flavin is between about 0.1 mM and 100 mM. In some embodiments, a concentration of flavin is between about 0.2 mM and 20 mM. In some embodiments, a concentration of flavin is about 0.1 mM, about 0.2 mM, about 0.3 mM, about 0.4 mM, about 0.5 mM, about 0.6 mM, about 0.7 mM, about 0.8 mM, about 0.9 mM, about 1.0 mM, about 1.1 mM, about 1.2 mM, about 1.3 mM, about 1.4 mM, about 1.5 mM, about 1.6 mM, about 1.7 mM, about 1.8 mM, about 2.9 mM, about 2.0 mM, about 2.1 mM, about 2.2 mM, about 2.3 mM, about 2.4 mM, about 2.5 mM, about 2.6 mM, about 2.7 mM, about 2.8 mM, about 2.9 mM, about 3.0 mM, about 3.1 mM, about 3.2 mM, about 3.3 mM, about 3.4 mM, about 3.5 mM, about 3.6 mM, about 3.7 mM, about 3.8 mM, about 3.9 mM, about 4.0 mM, about 4.1 mM, about 4.2 mM, about 4.3 mM, about 4.4 mM, about 4.5 mM, about 4.6 mM, about 4.7 mM, about 4.8 mM, about 4.9 mM, about 5.0 mM, about 5.5 mM, about 6.0 mM, about 6.5 mM, about 7.0 mM, about 7.5 mM, about 8.0 mM, about 8.5 mM, about 9.0 mM, about 9.5 mM, about 10.0 mM, about 10.5 mM, about 11.0 mM, about 11.5 mM, about 12.0 mM, about 12.5 mM, about 13.0 mM, about 13.5 mM, about 14.0 mM, about 14.5 mM, about 15.0 mM, about 15.5 mM, about 16.0 mM, about 16.5 mM, about 17.0 mM, about 17.5 mM, about 18.0 mM, about 18.5 mM, about 19.0 mM, about 19.5 mM, about 20.0 mM, about 20.5 mM, about 25.0 mM, about 30.0 mM, about 35.0 mM, about 40.0 mM, about 45.0 mM, about 50.0 mM, about 55.0 mM, about 60.0 mM, about 65.0 mM, about 70.0 mM, about 75.0 mM, about 80.0 mM, about 85.0 mM, about 90.0 mM, about 95.0 mM, or about 100.0 mM.

Optical Properties

In some embodiments, a flavin compounds absorb light in the visual spectrum. In some embodiments, a flavin compound absorbs light between 330 nm and 770 nm.

In some embodiments, a flavin compound absorbs blue light. In some embodiments, a flavin compound absorbs light between 330 nm and 470 nm. In some embodiments, a flavin compound absorbs light between 350 nm and 450 nm.

Administration

Silk fibroin hydrogels of the present disclosure may be administered to a site or subject by any appropriate route.

In some embodiments, a silk fibroin solution is administered with a solution of a flavin compound, such as a riboflavin solution. In some embodiments, a silk fibroin solution is mixed or blended with a solution of a flavin compound. In some embodiments, a silk fibroin solution is separately administered from a solution of a flavin compound.

In some embodiments, silk fibroin solutions with or without a flavin compound such as riboflavin are first gelled or partially gelled prior to administration.

To give but a few examples, exemplary modes of administration to a subject include, but are not limited to, topical, implant, injection, infusion, spray, instillation, implantation, or ingestion. "Injection" includes, without limitation, intravenous, intramuscular, intraarterial, intrathecal, intraventricular, intracapsular, intraorbital, intracardiac, intradermal, intraperitoneal, transtracheal, transocular, subcutaneous, subcuticular, intraarticular, sub capsular, subarachnoid, intraspinal, intracerebro spinal, and intrasternal injection and infusion.

In some embodiments, solutions or silk fibroin and/or a flavin compound are configured to be injectable.

In some embodiments, a viscosity of an injectable composition is modified by using a pharmaceutically acceptable thickening agent. In some embodiments, a thickening agent, for example, is methylcellulose, xanthan gum, carboxymethyl cellulose, hydroxypropyl cellulose, carbomer, or combination thereof. A preferred concentration of the thickener depends upon a selected agent and viscosity for injection.

Ocular Prosthesis

In some embodiments, silk fibroin hydrogels of the present disclosure are safely incorporated in vivo. In some embodiments, silk fibroin hydrogels are incorporated in or on a surface of corneal tissue.

In some embodiments, solutions as described herein are applied to an ocular surface. In some embodiments, gels as described herein are applied to an ocular surface.

In some embodiments, covalent crosslinks are formed between an eye and an ocular prosthesis, for example between silk fibroin hydrogels and corneal collagen.

In some embodiments, ocular prosthesis adhere to a surface of an eye. In some embodiments, ocular prosthesis remain adhered and intact following vigorous washing steps.

In some embodiments, silk fibroin-based hydrogels possess a three-dimensional (3D) structure. In some embodiments, silk fibroin-based hydrogels are moldable, for example, provided silk fibroin-based hydrogels may be shaped into optical components. In some embodiments, silk fibroin-based hydrogels are altered by laser shaping or writing. In some embodiments, silk fibroin-based hydrogels are mechanically manipulated.

In some embodiments, silk fibroin-based hydrogels are useful in the formation of optical components. In some embodiments, silk fibroin-based hydrogels are characterized in that they are capable of being shaped and/or molded to form convex or concave geometries that enable the formation of optical components, such as a lens. In some embodiments, silk fibroin-based hydrogels as provided herein are characterized by morphological features less than 100 nm.

Methods

In some embodiments, a method of providing, preparing, and/or manufacturing a silk fibroin-based hydrogels of the present disclosure includes crosslinking silk fibroin solutions.

Photocrosslinking

In some embodiments, a method of providing, preparing, and/or manufacturing a silk fibroin-based hydrogels of the present disclosure includes photocrosslinking silk fibroin solutions. In some embodiments, crosslinking silk includes steps of providing a silk solution and combining it with a flavin compound solution and exposing the combination to visible light.

In some embodiments, a combination of a silk solution and a Flavin solution is applied or deposited on a cornea of a subject. In some embodiments, crosslinking silk and corneal collagen includes steps of providing a silk solution, providing a Flavin-based solution, combining the silk and the Flavin solutions, applying a combination to a corneal surface and exposing the applied combination to visible light.

In some embodiments, such a crosslinking step may be carried out by exposing a silk fibroin-based hydrogel as provided herein with a crosslinking agent, such as a flavin compound to visible light.

In some embodiments, photocrosslinking occurs when a silk fibroin combined with, impregnated with, infused with, mixed with a flavin compound absorbs visible light.

In some embodiments, photocrosslinking occurs when a silk fibroin combined with, impregnated with, infused with, mixed with a flavin compound absorbs blue light. In some embodiments, a flavin compound absorbs light between 330 nm and 470 nm. In some embodiments, a flavin compound absorbs light between 350 nm and 450 nm.

In some embodiments, exposure of a silk solution with a flavin compound to visible light initiates crosslinking.

In some embodiments, increasing gelation occurs with increased exposure time. In some embodiments, exposure time is about 0 minutes to about 60 minutes. In some embodiments, exposure time is about 0 minutes to about 5 minutes. In some embodiments, exposure time is about 0 minutes to about 10 minutes. In some embodiments, exposure time is about 5 minutes to about 10 minutes. In some embodiments, exposure time is about 5 minutes to about 15 minutes. In some embodiments, exposure time is about 0 minutes to about 30 minutes. In some embodiments, exposure time is about 10 minutes to about 30 minutes. In some embodiments, exposure time is about 20 minutes to about 30 minutes. In some embodiments, exposure time is about 15 minutes to about 45 minutes. In some embodiments, exposure time is about 30 minutes to about 60 minutes.

In some embodiments, exposure time is about 0.5 hour, about 1.0 hour, about 1.5 hours, about 2.0 hours, about 2.5 hours, about 3.0 hours, about 3.5 hours, about 4.0 hours, about 4.5 hours, about 5.0 hours, about 5.5 hours, about 6.0 hours, about 6.5 hours, about 7.0 hours, about 7.5 hours, about 8.0 hours, about 8.5 hours, about 9.0 hours, about 9.5 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or longer.

In some embodiments, nanogelation of a silk fibroin solution to form silk fibroin-based hydrogels as provided herein occurs.

Methods of Tuning Gel Properties

In some embodiments, mixing or combining components or intermediates as disclosed herein with a polar organic solvent results in further gelation. In some embodiments, a polar organic solvent is or includes acetone, ethanol, methanol, isopropanol, or combinations thereof. In some embodiments, polar organic solvents drives the assembly of silk micelles into submicron-sized particles (<100 nm) to form silk fibroin-based hydrogels characterized as having optical transparency.

In some embodiments, matching, tuning, adjusting, and/or manipulating properties of a silk fibroin-based hydrogel include controlling, for example: by selecting a molecular weight of silk fibroin, by selecting a concentration of a silk fibroin solution, by selecting a solvent for a silk fibroin solution, by exposing silk fibroin-based hydrogels to polyamino carboxylic acids, such as (EDTA) at different concentrations and for different periods (e.g., durations), or by combinations thereof.

In some embodiments, provided technologies utilize simple methods and/or do not require or utilize organic solvents (particularly not volatile organic solvents). Also, in some embodiments, provided technologies prepare hydrogels in water. In some embodiments, provided technologies prepare hydrogels at sub-physiological pH and/or from solutions at sub-physiological pH. In some embodiments, such sub-physiological pH is at or near pH 6; in some embodiments, such sub-physiological pH is below 6. In some embodiments, the present disclosure encompasses the insight that use of buffered and/or salt-containing solutions (e.g., PBS) and/or solutions with higher pH (e.g., substantially physiological, or above, for example at, around, or above pH 7) can negatively impact mechanical properties of resulting hydrogels. Without wishing to be bound by any particular theory, the present disclosure proposes that use of such solutions can impact interactions between polymer chains in the hydrogel. For example, such interactions may be weaker in the presence of salt(s) than in water. According to some embodiments, provided water-prepared hydrogels show greater rigidity than those prepared from salt-containing or buffered solutions. In some embodiments, provided water-prepared hydrogels show improved cell viability and/or behavior as compared with those prepared from salt-containing or buffered solutions. In certain particular embodiments, crosslinking as described herein is performed on polymer (e.g., silk) solutions that are substantially free of salts and/or other buffering agents. In some crosslinking as described herein is performed on silk solutions in water.

In some embodiments, matching, tuning, adjusting, and/or manipulating mechanical properties of a silk fibroin-based hydrogel of the present disclosure is accomplished, at least in part, by selecting a molecular weight of a silk fibroin polypeptide. In some embodiments, a molecular weight of a silk fibroin polypeptide is in a range of molecular weights between about 10 kDa and about 350 kDa.

In some embodiments, matching, tuning, adjusting, and/or manipulating mechanical properties of a silk fibroin-based hydrogel of the present disclosure is accomplished, at least in part, by selecting a silk fibroin solution concentration. In some embodiments, a silk fibroin solution concentration is in a range of concentrations between about 0.1 mg/mL and about 20 mg/mL. In some embodiments, kinetics of gelation as well as plateau modulus can be controlled by adjusting a boiling time and a concentration.

In some embodiments, matching, tuning, adjusting, and/or manipulating mechanical properties, for example, a compressive modulus and/or a compressive strength of silk fibroin-based hydrogels may be tuned by adding polyamino carboxylic acids, such as (EDTA) at different concentrations and for different periods (e.g., durations).

Methods of Shaping and/or Molding Optical Components

In some embodiments, silk fibroin-based hydrogels possess a three-dimensional (3D) structure. In some embodiments, silk fibroin-based hydrogels are moldable, for example, provided silk fibroin-based hydrogels may be shaped into optical components. In some embodiments, silk fibroin-based hydrogels are altered by laser shaping or writing. In some embodiments, silk fibroin-based hydrogels are mechanically manipulated.

In some embodiments, silk fibroin-based hydrogels are useful in the formation of optical components. In some embodiments, silk fibroin-based hydrogels are characterized in that they are capable of being shaped and/or molded to form convex or concave geometries that enable the formation of optical components, such as a lens.

In summary, we have demonstrated a novel method of forming transparent, elastic, silk fibroin hydrogels in which excited riboflavin radicalizes tyrosine residues in the silk protein backbone, resulting in the formation of dityrosine complexes binding silk molecules together. This process uses only biologically and environmentally friendly materials. High resolution patterns of silk can be easily generated via photolithography using visible light rather than potentially damaging ultraviolet radiation. These silk hydrogels also show promise for the treatment of ocular injury and disease. The material can be selectively adhered to the cornea depending on the location of illumination, programmably changing the optical properties of the eye which would have a profound effect on vision. For ocular diseases that result in a deformed cornea including myopia and keratoconus, these films could be selectively applied to change the curvature of the eye to correct vision. The silk layer presented using this technique is not yet uniform enough for the precise optical corrections needed to restore visual acuity. However, silk fibroin, like other proteins, absorbs light strongly at wavelengths shorter than 200 nm. Excimer lasers used to correct myopia and hyperopia in LASIK procedures via the ablation of collagen, operate at 193 nm. In addition to collagen, this type of laser has been shown to ablate a wide variety of other polymeric materials. (See R. Srinivasan, B. Braren, 89 Chemical Reviews, 1303 (1989) hereby incorporated by reference in its entirety herein). Thus, we believe precise shaping of the silk gel layer on the cornea would be amenable to LASIK procedures. Complications due to LASIK procedures are permanent and can be debilitating. (See J. B. Randleman, R. D. Shah, 28 Journal of Refractive Surgery 8, 575 (2012) hereby incorporated by reference in its entirety herein). By performing LASIK procedures on silk prostheses instead of the native cornea, nearly risk-free LASIK vision correction should be possible even on patients with very thin corneas.

EXEMPLIFICATION

Example 1

The present example describes the Experimental Section in accordance with some embodiments of the present disclosure.

Silk Processing

Silk fibroin protein was isolated from silkworm cocoons via boiling in a 0.02 M sodium carbonate solution to remove the glue-like serecin protein that holds the cocoon together. The resulting fibroin was dissolved in 9.3 M lithium bromide, and dialyzed against deionized water for 72 hours. All silk used in rheology was lyophilized and subsequently dissolved to a concentration of 6% (wt/wt) in either deionized or deuterated water.

Example 2

Riboflavin

Preliminary gelation measurements were undertaken to find an optimum concentration of riboflavin. Highly soluble riboflavin 5'-monophosphate (FMN) was used to allow for the testing of a range of concentrations. Solutions of 0.2 mM, 2 mM, and 20 mM were tested on the rheometer as described above and it was found that 2 mM yielded the fastest crosslinking. This concentration is similar to the concentration of riboflavin used clinically for corneal crosslinking treatments (2.66 mM). (See L. A. Marquez, H. B. Dunford, 270 Journal of Biological Chemistry 51, 30434 (1995)).

Rheology

The evolution of the crosslinking process was monitored by gelling samples on a TA Instruments ARES-LS2 rheometer (TA Instruments, New Castle, Del.). Samples were analyzed in a parallel plate configuration with a quartz top plate and stainless steel base that was maintained at 37 degrees Celsius throughout testing. Illumination was provided by 3, 450 nm LEDs providing 18.7 $cm^{-2}$ mW) of light to the sample. Light from the LEDs passed through the top plate allowing the evolution of crosslinking to be measured in real time. Rheological measurements of different experimental treatments were found to have unequal variances by Bartlett's Test and the Fligner-Killeen test indicating that an analysis of variance (ANOVA) would be unreliable. Subsequent log-transformation of the data yielded approximately equal variance between the two groups (Bartlett's test p-value=0.96). A one-way ANOVA was conducted on the log-transformed data and significance between groups was assessed with Tukey's post-hoc test.

A concentration of riboflavin that led to the most efficient crosslinking was determined. The speed of crosslinking by measuring the elastic and storage moduli during gelation using a rheometer was tested. This setup allowed us to continuously monitor the gel's stiffness. It was found that a solution containing 2 mM of riboflavin led to the most rapid crosslinking.

Example 3

Illumination

The removal of illumination during testing immediately halted gel formation (FIG. 1, panel [A]) implying that the stiffness of these gels can be precisely controlled using only light exposure. Similarly, it was found that light along (without riboflavin) did not result in any sign of gel formation (FIG. 1, panel [B]).

Previous work on the mechanism of photocrosslinking collagen using riboflavin is conflicted. Some groups explain the effect as solely due to singlet oxygen production, (see A. S. McCall, S. Kraft, H. F. Edelhauser, G. W. Kidder, R. R. Lundquist, H. E. Bradshaw, Z. Dedeic, M. J. C. Dionne, E. M. Clement, G. W. Conrad, 51 Investigative Ophthalmology & Visual Science 1, 129 (2010) hereby incorporated by reference in its entirety herein), while others credit the production of tyrosyl radicals which can form dityrosine crosslinks. (See Y. Kato, K. Uchida, S. Kawakishi, 59 Photochemistry and Photobiology 3, 343 (1994) hereby incorporated by reference in its entirety herein).

Here, both potential mechanisms were investigated in silk by dissolving lyophilized silk protein in heavy water ($D_2O$), a radical oxygen promoter; sodium azide (NaAz), a radical oxygen scavenger; and superoxide dismutase (SOD), an enzyme that catalyzes the dismutation of superoxide anion radicals to oxygen or hydrogen peroxide. Gel formation was monitored using a rheometer with a quartz top plate which recorded the storage and shear moduli of the solution while under illumination.

It was found that the mechanism for photo crosslinking of silk fibroin is likely not due solely to the presence of singlet oxygen. Since singlet oxygen has a longer lifetime in $D_2O$, we would have expected to see faster stiffening when silk was dissolved in $D_2O$. However, there was no significant difference between the $D_2O$ group and the control (FIG. 1, panel [B]). Similarly, the addition of sodium azide which efficiently scavenges singlet oxygen should have sharply reduced the stiffness following illumination. Instead, it was found only a modest decrease in stiffness in the presence of sodium azide. These results imply that singlet oxygen does play a small role in silk fibroin crosslinking, but it is not the primary mechanism. Conversely, the addition of superoxide dismutase resulted in a more than six-fold increase in stiffness suggesting that the superoxide anion radical plays a strongly inhibitory role in this process.

A mechanism for riboflavin photocrosslinking in collagen has been suggested by Kato et al. (See Y. Kato, K. Uchida, S. Kawakishi, 59 Photochemistry and Photobiology 3, 343 (1994) hereby incorporated by reference in its entirety herein). Their hypothesis is that photoexcited riboflavin (RF*) strips electrons from tyrosine residues (T) in collagen forming tyrosyl radicals (T⁻). Two tyrsosyls are then able to form a single dityrosine complex (T-T) chemically crosslinking collagen protein backbones. Superoxide anion radicals ($O_2^-$) are an intermediate species in this reaction and have been shown to heal radical tyrosine which would prevent the formation of dityrosine bonds. (See E. P. L. Hunter, M. F. Desrosiers, M. G. Simic, 6 Free Radical Biology and Medicine 6, 581 (1989) hereby incorporated by reference in its entirety herein). Other researchers have noted dityrosine as a photoproduct of illuminating riboflavin in vivo. (See E. Silva, S. Furst, A. Edwards, 62 Photochemistry and Photobiology 6, 5 (1995) hereby incorporated by reference in its entirety herein).

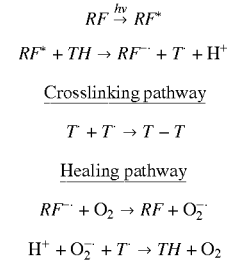

$$RF \xrightarrow{h\nu} RF^*$$

$$RF^* + TH \rightarrow RF^{-\cdot} + T^\cdot + H^+$$

Crosslinking pathway $$T^\cdot + T^\cdot \rightarrow T-T$$

Healing pathway $$RF^{-\cdot} + O_2 \rightarrow RF + O_2^-$$

$$H^+ + O_2^- + T^\cdot \rightarrow TH + O_2$$

Dityrosine Fluorescence

Riboflavin and water were added to a silk fibroin solution to a concentration of 5% (wt/wt) silk and 2 mM riboflavin. A control solution of 5% silk was also prepared without riboflavin. 50 μL of either the riboflavin or control solution was pipetted into an opaque 96-well plate. Wells were exposed to light for 0, 20, 40, or 60 minutes. Shadowing from the walls of the well make it difficult to estimate the total light exposure over this period. Half of the riboflavin containing gels were rinsed in deionized water over the next 48 hours. Following rinsing, fluorescence spectra were collected of all wells using a Spectramax M2 (Molecular Devices, Sunnyvale, Calif.) micro-plate fluorescence spectrometer. Excitation wavelengths of 310 nm and 450 nm were used to look for dityrosine and riboflavin fluorescence respectively.

To confirm the presence of dityrosine in silk/riboflavin gels their fluorescence spectra (FIG. 1, panel [C]) was examined. Under excitation with 310 nm light, dityrosine fluoresces strongly around 400 nm. (See L. A. Marquez, H. B. Dunford, 270 Journal of Biological Chemistry 51, 30434 (1995) hereby incorporated by reference in its entirety herein). Riboflavin has a broad absorption peak from 350 to 450 nm which might obscure the dityrosine fluorescence, so gels were rinsed with water to remove the riboflavin following gel formation. We found evidence of a clear dityrosine fluorescence peak in the rinsed gels that was not present in silk alone. The un-rinsed gels show both a small dityrosine peak as well as a small peak at 532 nm which is indicative of riboflavin fluorescence. In the un-rinsed samples the dityrosine fluorescence at 410 nm is absorbed by the riboflavin in the gel resulting in the detection of both weak dityrosine and riboflavin fluorescence.

Observed mechanical properties of riboflavin photocrosslinked gels also support the proposed mechanism. Silk/riboflavin gels have a large shear modulus coupled with a negligible storage modulus. Enzymatically crosslinked silk fibroin hydrogels form dityrosine bonds through the action of horseradish peroxidase show similar elastic properties. (See B. P. Partlow, C. W. Hanna, J. Rnjak-Kovacina, J. E. Moreau, M. B. Applegate, K. A. Burke, B. Marelli, A. N. Mitropoulos, F. G. Omenetto, D. L. Kaplan, Advanced Functional Materials, 4615-4624 (2014) hereby incorporated by reference in its entirety herein).

Photolithography

Since both riboflavin and light are required for hydrogel formation it was hypothesized that it would be possible to generate high resolution patterns of silk gel using photolithography. To do so, a photomask of a U.S. Air Force resolution test pattern printed on mylar with a nominal resolution of 20 μm was used.

A mylar photomask with a United States Air Force resolution test pattern was obtained from Advance Reproductions (North Andover, Mass.). Silk solution with riboflavin was drop cast onto a glass slide and manually spread into a uniform layer. The photomask was placed 1 mm above the surface of the liquid solution and 15 J cm$^{-2}$ of light provided from above. Following illumination, the glass slide was placed in deionized water and agitated gently for 5 minutes. The slide was removed from the water and allowed to dry for 12 hours prior to imaging.

Figure 2:
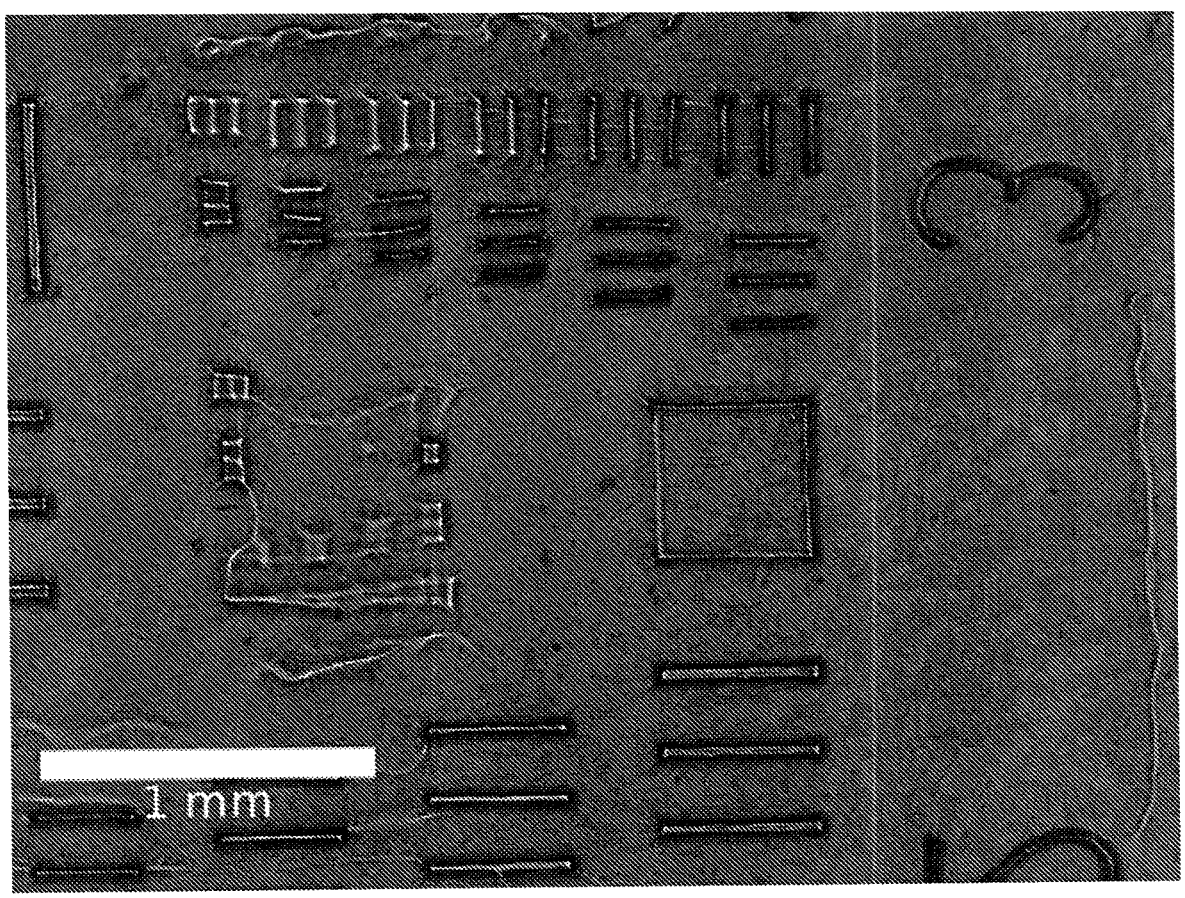
FIG. 2. Brightfield microscope image of a high-resolution pattern of silk gel produced by photolithography. Blue light was passed through a photomask and used to illuminate a mixture of silk and riboflavin. Pattern silk gels were formed with a resolution of about 50 Pattern silk gels were formed with a resolution of down to about 20 µm.

Illumination using 450 nm LEDs was provided from above through the mask. After illumination the pattern could be clearly seen in the gel due to photobleaching of the riboflavin. The sample was placed in deionized water and gently agitated for 5 minutes to remove any unpolymerized silk. (See S. Kim, B. Marelli, M. A. Brenckle, A. N. Mitropoulos, E. Gil, K. Tsioris, H. Tao, D. L. Kaplan, F. G. Omenetto, 9 Nat. Nanotechnol., 306 (2014) hereby incorporated by reference in its entirety herein). A clear pattern transfer after washing and, following drying in ambient conditions was observed. Polymerized silk was tightly bound to the substrate (FIG. 2). Using this rudimentary system the resolution ~20 µm resolution, which is the same as the resolution of the photomask was achieved. It is likely that the resolution of these patterns could be significantly improved using a higher resolution mask and a more sophisticated apparatus and further optimizing the development of the photoexposed sample.

Example 4

Corneal Adhesion

To test whether photocrosslinked silk hydrogels could be adhered to corneal collagen, silk films impregnated with FMN and SOD were adhered to enucleated porcine eyes. Silk fibroin films were cut into 1 cm disks and applied to eyes with the corneal epithelium removed. Thickness of the silk fibroin films on the eye was measured by optical coherence tomography (OCT) immediately after application to the eye, following light exposure, and after a vigorous rinse in phosphate buffered saline (PBS).

Riboflavin and SOD impregnated silk films along with silk and SOD films without riboflavin were prepared by mixing the components with liquid silk solution. Riboflavin was added to a concentration of 0.2 mM and SOD added at a concentration of 1.7 U/mL. Water was added to each solution to bring the concentration of silk down to 6% (wt/wt). The resulting solution was cast onto a (poly) dimethylsiloxane mold and allowed to crosslinking. Fresh porcine eyes were obtained from Animal Technologies (Tyler, Tex.). 25% ethanol was applied to each eye to facilitate the removal of the corneal epithelium. Loosened epithelium was fully removed by mechanical debridement with a razor blade. Once the cornea was cleared of epithelium, a 1 cm diameter disk of silk film was applied to the cornea. Eyes were then exposed to 15 cm$^{-2}$ J of 450 nm light over 20 minutes. During illumination phosphate buffered saline (PBS) was gently applied to the eye every 5 minutes to keep it moist. Samples were imaged using optical coherence tomography (OCT) before application to the eye, before illumination, after illumination, and following a vigorous rinsing with 3 mL PBS. Eyes were fixed in formalin for sectioning and staining with hemotoxylin and eosin. Silk thickness in the OCT images were measured manually using ImageJ. For statistical analysis data were averaged across all positions on the eyes. Separate multiple comparison tests were performed at each time point. ANOVAs were performed on the dry film and pre-light time points followed by Tukey's post-hoc test. After fitting, the residuals of the post-light and post-wash time points were not normally distributed so the non-parametric Kruskal-Wallis test was used. Differences between groups were evaluated via Dunn's test using the Holm p-value adjustment method.

Figure 3:
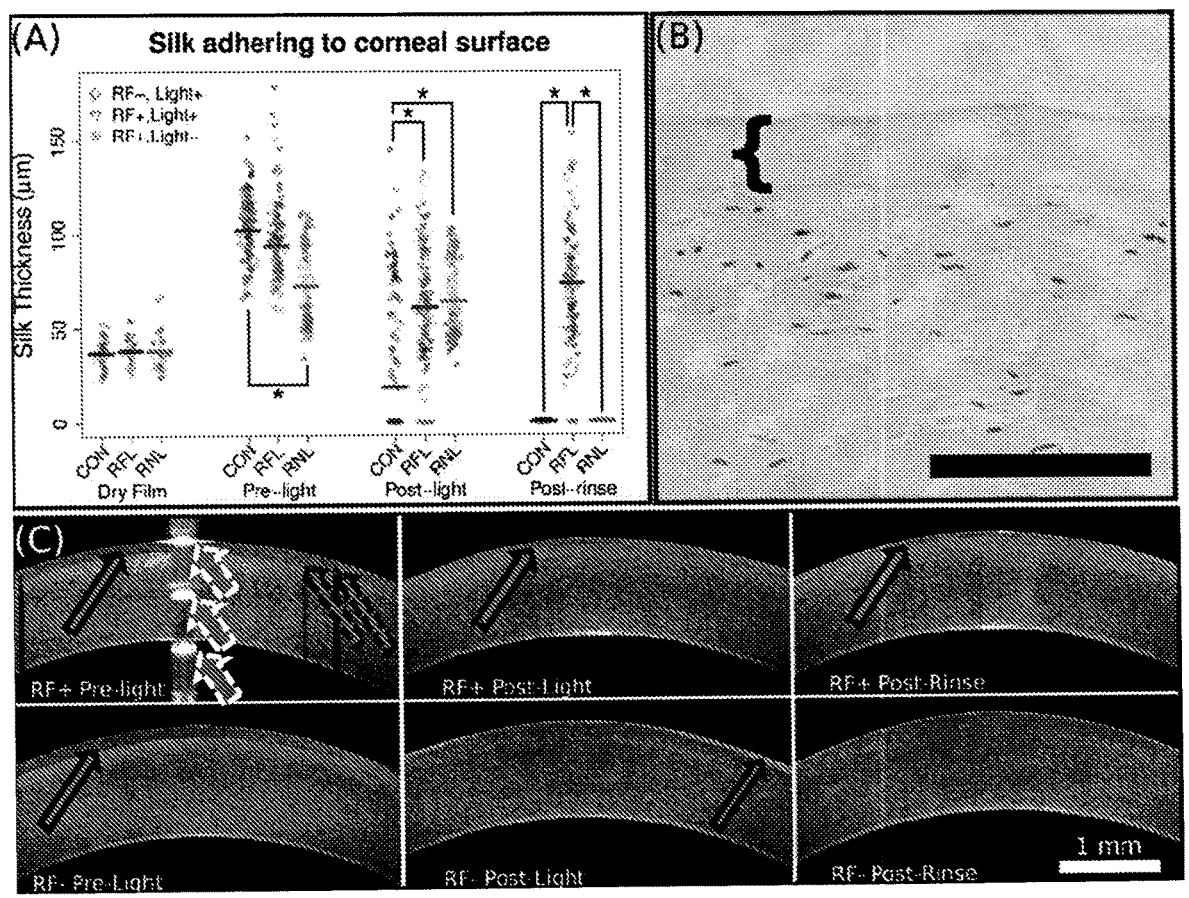
FIG. 3 Silk/Cornea adherence.

Both the riboflavin impregnated films as well as the control films without riboflavin were found to adhere to the eyes initially (FIG. 3, panel [A]) because silk films are very sticky as they begin to dissolve. However, silk films without riboflavin quickly degrade under additional wetting leaving the cornea largely bare. Conversely, the riboflavin films imaged post illumination showed little indication of wear and remained adhered to the surface of the eye (FIG. 3, panel [C]) even after vigorous rinsing with PBS. Control samples containing riboflavin but not exposed to light were easily removed from the eye by rinsing with PBS. Histologic inspection of the eyes revealed that the silk gel was smoothly attached to the corneal collagen without any evidence of separation (FIG. 3, panel [B]).

Figure 4:
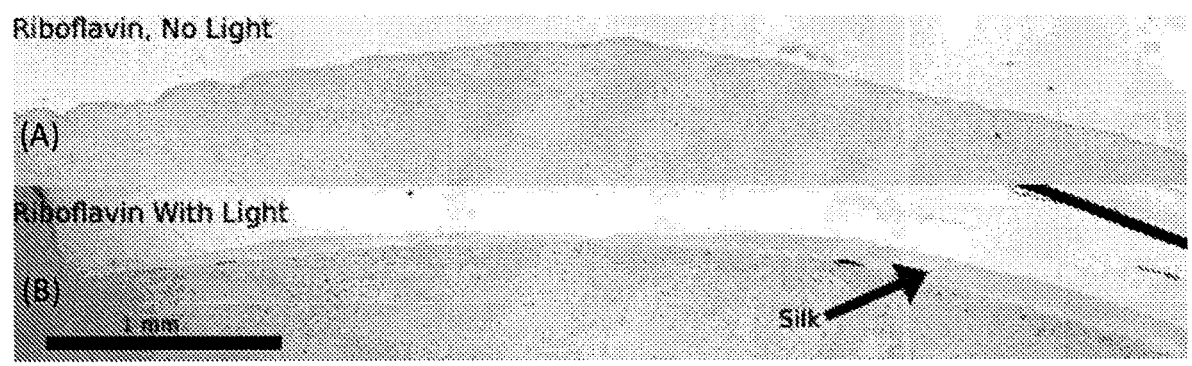
FIG. 4 Histologic section of porcine corneas.

Histologic section of porcine corneas that were treated with silk doped with riboflavin but were not exposed to light showed no silk film remaining on the unexposed corneas. (FIG. 4 at panel [A]). Histologic section of porcine corneas that were treated with silk doped with riboflavin and exposed to light showed that a film of silk was present on the areas of the cornea exposed to light. (FIG. 4 at panel [B]).

OTHER EMBODIMENTS AND EQUIVALENTS

While the present disclosures have been described in conjunction with various embodiments, and examples, it is not intended that they be limited to such embodiments, or examples. On the contrary, the disclosures encompass various alternatives, modifications, and equivalents, as will be appreciated by those of skill in the art. Accordingly, the descriptions, methods and diagrams of should not be read as limited to the described order of elements unless stated to that effect.

Although this disclosure has described and illustrated certain embodiments, it is to be understood that the disclosure is not restricted to those particular embodiments. Rather, the disclosure includes all embodiments, that are functional and/or equivalents of the specific embodiments, and features that have been described and illustrated. Accordingly, for example, methods and diagrams of should not be read as limited to a particular described order or arrangement of steps or elements unless explicitly stated or clearly required from context (e.g., otherwise inoperable). Moreover, the features of the particular examples and embodiments, may be used in any combination. The present disclosure therefore includes variations from the various examples and embodiments, described herein, as will be apparent to one of skill in the art.

What is claimed is:

1. A method, comprising:
   providing a mixture comprising silk fibroin and a flavin compound;
   contacting the mixture to corneal tissue; and
   exposing the mixture to visible light to induce dityrosine crosslinks in the silk fibroin to form a silk fibroin hydrogel that adheres to the corneal tissue.

2. The method of claim 1, wherein the step of providing the mixture comprises steps of: providing a solution comprising silk fibroin; and combining the silk fibroin solution with a solution comprising a flavin compound.

3. The method of claim 1, wherein the mixture is an aqueous mixture.

4. The method of claim 1, further comprising a step of selectively shaping the silk fibroin hydrogel adhered to the corneal tissue.

5. The method of claim 1, wherein the flavin compound is riboflavin or a flavin-mononucleotide (FMN).

6. The method of claim 1, following formation of the silk fibroin hydrogel further comprising a step of rinsing the silk fibroin hydrogel to remove residual flavin compound.

7. The method of claim 1, wherein the visible light is in a wavelength range of about 330 nm to about 470 nm.

8. The method of claim 1, wherein the step of exposing the mixture comprises selectively exposing the mixture to visible light to induce dityrosine crosslinks in the silk fibroin to selectively form a silk fibroin hydrogel that selectively adheres to the corneal tissue.

9. The method of claim 2, wherein the silk fibroin solution has a concentration in a range of about 0.1 mg/mL and 15 mg/mL.

10. The method of claim 1, wherein the silk fibroin hydrogel has at least one characteristic selected from the group consisting of:
  recovers from a shear strain of at least 100% without showing an indication of a plastic deformation;
  substantially transparent to wavelengths above 200 nm;
  exhibits negligible absorbance above 290 nm so that it is optically clear;
  recovers from a compressive strain of at least 75% without showing an indication of a plastic deformation;
  a storage modulus value that is between about 50 Pa and about 100 kPa;
  a tangent modulus of about 200 Pa to about 400 kPa;
  configured to be injectable;
  a thickness that is substantially maintained with rinsing, and
  substantially adheres to corneal tissue with rinsing.

* * * * *

UNITED STATES PATENT AND TRADEMARK OFFICE
CERTIFICATE OF CORRECTION

PATENT NO. : 11,833,272 B2  
APPLICATION NO. : 16/063479  
DATED : December 5, 2023  
INVENTOR(S) : Omenetto et al.

Page 1 of 1

It is certified that error appears in the above-identified patent and that said Letters Patent is hereby corrected as shown below:

In the Specification

In Column 9, Line 42, After "50", insert --µm.--

In Column 9, Line 58, After "100", insert --µm.--

Signed and Sealed this  
Seventh Day of May, 2024

Katherine Kelly Vidal  
*Director of the United States Patent and Trademark Office*